United States Patent [19]

Sallmann

[11] 4,447,431
[45] May 8, 1984

[54] TRI-SUBSTITUTED IMIDAZOLE DERIVATIVES, PHARMACEUTICAL PREPARATIONS CONTAINING THEM, AND THEIR USE

[75] Inventor: Alfred Sallmann, Bottmingen, Switzerland

[73] Assignee: Ciba-Geigy Corporation, Ardsley, N.Y.

[21] Appl. No.: 425,603

[22] Filed: Sep. 28, 1982

Related U.S. Application Data

[62] Division of Ser. No. 285,231, Jul. 20, 1981.

[30] Foreign Application Priority Data

Jul. 25, 1980 [CH] Switzerland ............... 5715/80

[51] Int. Cl.³ .............. A61K 31/415; A61K 31/44; A61K 31/535; C07D 401/04
[52] U.S. Cl. .................. 424/246; 544/364; 544/370; 544/58.4; 544/122; 544/131; 544/139; 544/295; 544/296; 544/333; 544/360; 546/193; 546/194; 546/210; 546/256; 546/278; 548/200; 548/215; 548/336; 548/342; 260/243.3; 260/244.4; 260/245.6; 424/59; 424/60; 424/248.4; 424/250; 424/251; 424/263; 424/267; 424/270; 424/272; 424/273 R
[58] Field of Search .............. 548/200, 215, 336, 342; 546/193, 194, 210, 256, 278; 544/58.4, 122, 131, 139, 295, 296, 333, 364, 360, 370; 542/427, 436, 440; 424/59, 60, 246, 248.4, 250, 251, 263, 267, 270, 272, 273 R; 260/243.3, 244.4, 245.6

[56] References Cited

U.S. PATENT DOCUMENTS 4,372,964 2/1983 Whitney ............... 546/256 X

FOREIGN PATENT DOCUMENTS 1469532 5/1977 United Kingdom .

OTHER PUBLICATIONS

Bader et al., Helvetica Chemica Acta, vol. 61, (1978), pp. 286–304.
Bader et al., Chimia, vol. 29, (1975), pp. 264–266.
Nyitrai et al., Acta. Chim. Acad. Hung., (1978), vol. 97, No. 1, pp. 91–99.

Primary Examiner—Richard Raymond
Attorney, Agent, or Firm—Michael W. Glynn

[57] ABSTRACT

The invention relates to novel tri-substituted imidazole derivatives, especially compounds of the general formula I

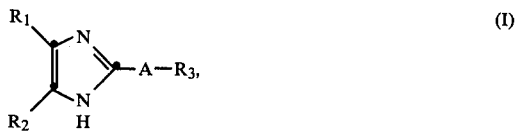

in which
R₁ and R₂ represent, independently of each other, carbocyclic aryl and heteroaryl,
A represents a divalent hydrocarbon radical, and
R₃ represents carboxy, esterified carboxy or amidated carboxy, their isomers and their salts, especially pharmaceutically acceptable salts, with the proviso that, if A represents methylene or ethylidene and R₃ represents ethoxycarbonyl, at least one of the radicals R₁ and R₂ is different from phenyl, and the further proviso that, if A represents ethylidene and R₃ represents carboxy, at least one of the radicals R₁ and R₂ is different from phenyl, p-methoxyphenyl and p-chlorophenyl, processes for their manufacture, pharmaceutical preparations containing such compounds, and their use, for example as active substances in medicaments.

The compounds of the formula I can be used as skin phlogistatics, sun-screening agents and antiviral agents.

17 Claims, No Drawings

TRI-SUBSTITUTED IMIDAZOLE DERIVATIVES, PHARMACEUTICAL PREPARATIONS CONTAINING THEM, AND THEIR USE

This is a divisional of application Ser. No. 285,231 filed on July 20, 1981.

The invention relates to novel tri-substituted imidazole derivatives, especially compounds of the general formula I

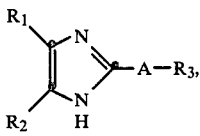

in which $R_1$ and $R_2$ represent, independently of each other, carbocyclic aryl and heteroaryl, A represents a divalent hydrocarbon radical, and $R_3$ represents carboxy, esterified carboxy or amidated carboxy, their isomers and their salts, especially pharmaceutically acceptable salts, with the proviso that, if A represents methylene or ethylidene and $R_3$ represents ethoxycarbonyl, at least one of the radicals $R_1$ and $R_2$ is different from phenyl, and the further proviso that, if A represents ethylidene and $R_3$ represents carboxy, at least one of the radicals $R_1$ and $R_2$ is different from phenyl, p-methoxyphenyl and p-chlorophenyl, processes for their manufacture, pharmaceutical preparations containing such compounds, and their use, for example as active substances in medicaments.

Carbocyclic aryl is, for example, monocyclic carbocyclic aryl, such as optionally substituted phenyl.

Heteroaryl is, for example, monocyclic, preferably 5- or 6-membered, heteroaryl, wherein at least one ring member represents a hetero atom, such as a nitrogen, oxygen or sulphur atom, wherein a nitrogen atom can also be optionally in oxidised form. Such 5-membered radicals are, for example, pyrrolyl, such as 2-pyrrolyl, furyl, such as 2-furyl, thienyl, such as 2- or 3-thienyl.

As 6-membered heteroaryl there come into consideration, for example, pyridyl, such as 2-, 3- or 4-pyridyl, 1-oxidopyridyl, such as 1-oxido-3-pyridyl or 1-oxido-4-pyridyl, and pyrimidyl, such as 2-pyrimidyl.

As substituents of carbocyclic aryl, such as phenyl, and of heteroaryl, such as pyridyl or 1-oxidopyridyl, there come into consideration, for example, halogen, lower alkyl, hydroxy, lower alkoxy and/or acyloxy. Acyloxy is derived, for example, from an organic carboxylic acid and represents, for example, lower alkanoyloxy.

A hydrocarbon radical A is, for example, a divalent aliphatic, cycloaliphatic or cycloaliphatic-aliphatic hydrocarbon radical.

As divalent aliphatic hydrocarbon radicals there come into consideration, for example, lower alkylene, lower alkylidene, lower alkenylene or lower alkenylidene. Divalent cycloaliphatic hydrocarbon radicals are, for example, monocyclic 3- to 8-membered cycloalkylenes or cycloalklidenes. Cycloaliphatic-aliphatic hydrocarbon radicals are, for example, those having, as the cycloaliphatic radical, a monocyclic 3- to 8-membered cycloaliphatic radical and, as the aliphatic radical, lower alkylidene, such as cycloalkyl-lower alkylidene.

Esterified carboxy is, for example, carboxy esterified by an optionally substituted aliphatic, cycloaliphatic or aromatic alcohol. An aliphatic alcohol is, for example, a lower alkanol, such as methanol, ethanol, propanol, isopropanol, n-butanol, sec.- or tert.-butanol, whilst there comes into consideration as cycloaliphatic alcohol, for example, a 3- to 8- membered cycloalkanol, such as cyclopentanol, cyclohexanol or cycloheptanol. As substituents of such lower alkanols and cycloalkanols there come into consideration, for example, hydroxy, mercapto, optionally substituted phenyl, lower alkoxy, phenyl-lower alkoxy optionally substituted in the phenyl moiety, lower alkylthio phenyl-lower alkylthio optionally substituted in the phenyl moiety, hydroxy-lower alkoxy, lower alkoxy-lower alkoxy, phenyl-lower alkoxy-lower alkoxy optionally substituted in the phenyl moiety, carboxy-lower alkoxy, lower alkoxycarbonyl-lower alkoxy, lower alkoxycarbonyl-lower alkoxy substituted by optionally substituted phenyl, or lower alkanoyloxy. An aromatic alcohol is, for example, a phenol or a heterocyclic alcohol each of which may optionally be substituted by lower alkyl, lower alkoxy, halogen and/or trifluoromethyl, especially hydroxypyridine, for example 2-, 3- or 4-hydroxypyridine.

Amidated carboxy is, for example, carbamoyl, carbamoyl mono-substituted by hydroxy, amino or optionally substituted phenyl, carbamoyl mono- or di-substituted by lower alkyl, or carbamoyl di-substituted by 4- to 7-membered alkylene or 3-aza-, 3-lower alkyl-aza-, 3-oxa- or 3-thiaalkylene. As examples, there may be mentioned carbamoyl, N-mono- or N,N-di-lower alkylcarbamoyl, such as N-methyl-, N-ethyl, N,N-dimethyl-, N,N-diethyl- or N,N-dipropylcarbamoyl, pyrrolidino- or piperidinocarbonyl, morpholino-, piperazino- or 4-methylpiperazinocarbonyl and thiomorpholinocarbonyl, anilinocarbonyl or anilinocarbonyl substituted by lower alkyl, lower alkoxy and/or halogen.

In the present description, by "lower" organic radicals and compounds there is to be understood preferably those that contain up to and including 7, especially up to and including 4, carbon atoms.

The general definitions used hereinbefore and hereinafter have, within the scope of the present application, especially the following meanings:

Halogen is, for example, halogen having up to and including an atomic number of 35, such as fluorine, chlorine or bromine, furthermore iodine.

Lower alkyl is, for example, methyl, ethyl, n-propyl, isopropyl, n-butyl, isobutyl, sec.-butyl, tert.-butyl, or a pentyl, hexyl or heptyl radical.

Lower alkoxy is, for example, methoxy, ethoxy, n-propoxy, isopropoxy, n-butoxy, isobutoxy, sec.-butoxy or tert.-butoxy.

Lower alkylthio is, for example, methyl-, ethyl-, n-propyl-, isopropyl-, n-butyl-, isobutyl-, sec.-butyl- or tert.-butylthio.

Phenyl-lower alkoxy is, for example, phenylmethoxy, phenylethoxy, or phenylpropoxy.

Phenyl-lower alkylthio is, for example, benzyl-, phenylethyl- or phenylpropylthio.

Hydroxy-lower alkoxy is, for example, hydroxyethoxy, hydroxypropoxy or 1,2-dihydroxypropoxy.

Lower alkoxy-lower alkoxy is, for example, methoxyethoxy, ethoxyethoxy, methoxypropoxy or methoxybutoxy.

Phenyl-lower alkoxy-lower alkoxy is, for example, 2-benzyloxyethoxy or 2-(2-phenylethoxy)-ethoxy.

Lower alkanoyloxy is, for example, acetoxy, propionyloxy, butyryloxy, isobutyryloxy, sec.-butyryloxy or tert.-butyryloxy.

Lower alkylene is, for example, straight-chained, such as methylene, ethylene, 1,3-propylen or 1,4-butylene, or branched, such as 1,2-propylene, 1,3- or 1,3-(2-methyl)-propylene or 1,2-butylene.

Lower alkylidene contains a tertiary or, preferably, a quaternary carbon atom and is, for example, ethylidene or 1,1- or 2,2-propylidene, and also 1,1- or 2,2-butylidene or 1,1-, 2,2- or 3,3-pentylidene.

Lower alkenylene is, for example, ethenylene, 1,2- or 1,3-propenylene or 1,2-, 1,3- or 1,4-buten-2-ylene.

Lower alkenylidene is, for example, ethenylidene, 1,1-propen-1-ylidene, 1,1-propen-2-ylidene, and also butenylidene, such as 1,1-buten-3-ylidene.

Cycloalkylene is, for example, cyclopropylene, 1,2- or 1,3- cyclobutylene, 1,2- 1,3- or 1,4-cyclopentylene, and also cyclohexylene.

Cycloalkylidene is, for example, cyclopropylidene, cyclobutylidene, cyclopentylidene or cyclohexylidene.

Cycloalkyl-lower alkylidene is, for example, cyclopropyl-, cyclobutyl-, cyclopentyl- or cyclohexyl-methylene, -ethylidene or -propylidene, and also cyclohexyl-butylidene.

Carboxy-lower alkoxy is, for example, carboxymethoxy, 2-carboxyethoxy, 2-, 3-carboxypropyloxy, 1-carboxy-2-propyloxy, 2-, 3- or 4-carboxy-n-butyloxy, 1carboxy-2-methylpropyl-3-oxy or 1-carboxy-2-methyl-propyl-2-oxy.

Lower alkoxycarbonyl-lower alkoxy contains in the lower alkoxy part, independently of each other the meanings given under lower alkoxy.

Salts of compounds of the formula I according to the invention are preferably pharmaceutically acceptable salts, such as pharmaceutically acceptable acid addition salts, and/or, if $R_3$ represents carboxy and/or $R_1$ and $R_2$, independently of each other, represent phenyl or heteroaryl each substituted by hydroxy, internal salts or salts with bases. Suitable acid addition salts are, for example, salts with inorganic acids, such as a mineral acid, with sulphamic acids, such as cyclohexylsulphamic acid, with organic carboxylic acids, such as lower alkanecarboxylic acids, optionally unsaturated dicarboxylic acids, with carboxylic acids substituted by hydroxy and/or oxo, or with sulphonic acids, for example sulphates or hydrohalides, such as hydrobromides or hydrochlorides, oxalates, malonates, fumarates or maleinates, tartrates, pyruvates or citrates, or sulphonates, such as methane-, benzene- or p-toluenesulphonate.

Suitable salts with bases are, for example, alkali metal or alkaline earth metal salts, for example sodium, potassium or magnesium salts, pharmaceutically acceptable transition metal salts, such as zinc or copper salts, or salts with ammonia or of substituted organic amines, such as cyclic amines, for example morpholine, thiomorpholine, piperidine, pyrrolidine, such as mono-, di- and tri-lower alkylamines or mono-, di- and tri-hydroxy-lower alkylamines, for example mono-, di- and tri-ethanolamine. Mono-lower alkylamines are, for example, ethylamine or tert.-butylamine. Di-lower alkylamines are, for example, diethylamine or diisopropylamine, and, as tri-lower alkylamine, there comes into consideration, for example, triethylamine.

The novel compounds of the formula I and their pharmaceutically acceptable salts have valuable pharmacological properties. In particular, for example when administered locally, they possess a pronounced anti-inflammatory action.

This property can be demonstrated, for example according to the method developed by G. Tonelli, L. Thibault, Endocrinology 77, 625 (1965), by inhibition of the oedema induced by croton oil in the ears of normal rats, in a dosage range of from approximately 1 to approximately 100 mg/ml.

The excellent inflammation-inhibiting action is similarly apparent in the ultraviolet rays dermatitis inhibition test in guinea pigs [methodology: Weirich, E. G.; Longauer, J.; Kirkwood, A. H.; Dermatologica 152, 87–99 (1976)] and by means of the croton oil dermatitis inhibition test in rabbits [methodology: Weirich, E. G.; Longauer, J.; Kirkwood, A. H.; Arch. Derm. Res. 259, 141–9 (1977)] in each case in a dosage range of from approximately 0.01 to approximately 1.0% W/W in the case of topical administration of a corresponding solution. Furthermore, the compounds according to the invention show a pronounced inhibitory action in the hyperplasia inhibition test in guinea pigs in a dosage range of approximately from 0.01 to 1.0% W/W in the case of topical administration [methodology: Weirich, E. G.; Longauer, J.; Kirkwood, A. H.; Dermatologica 151, 321–332 (1975)]. The substances have also been subjected to an activity test in humans. In the skin vasoconstriction solution test a considerable vasoconstrictive effect could be detected in a dosage range of approximately from $1 \times 10^{-5}$ to $1 \times 10^{-1}$ W/W [methodology: Weirich, E. G.; Lutz, U.; Dermatologica 155, 328–334 (1977)].

Furthermore, the compounds according to the invention are distinguished by marked effects against some strains of virus. For example, in experiments on guinea pigs that have been infected with HVH 2/Angelotti [methodology: B. Lukas et al., Arch. Ges. Virusforsch. 44, 153–5 (1974) and 49, 1–11 (1975)], a rapid regression or complete reduction of the symptoms caused by *Herpes genitalis* is detected after intravaginal administration of 0.1 ml of a gel with 0.2% concentration twice daily for 5 days.

The compounds of the formula I according to the invention are therefore suitable as medicaments, especially external (topical) skin phlogistatics for the treatment of inflammatory dermatoses of whatever origin, such as in the case of mild skin irritations, contact dermatitis, exanthems, burns, and as mucous membrane phlogistatics for the treatment of inflammation of the mucous membranes, for example of the eyes, nose, lips, mouth and the genital and anal region. The compounds can also be used as sun-screening agents and as antiviral agents, for example anti-herpes agents.

The present invention relates also to the use of the compounds according to the invention and salts thereof and to pharmaceutical preparations containing them, and their use for the treatment of inflammations, for example of inflammatory disorders of the most varied origin, and for the manufacture of medicaments.

The invention relates, for example, to compounds of the formula I in which, on the one hand, $R_1$ and $R_2$ represent, independently of each other, phenyl, and/or phenyl substituted by halogen, lower alkyl, hydroxy, lower alkoxy, and/or lower alkanoyloxy or in which, on the other hand, one of the radicals $R_1$ and $R_2$ represents pyrrolyl, furyl, thienyl, pyridyl, 1-oxidopyridyl or pyrimidyl each of which can be unsubtituted or substituted by halogen, lower alkyl, hydroxy, lower alkoxy and/or lower alkanoyloxy, and the other represents phenyl, pyrrolyl, furyl, thienyl, pyridyl, 1-oxidopyridyl, or pyrimidyl each of which can be unsubstituted or substituted by halogen, lower alkyl, hydroxy, lower alkoxy, and/or lower alkanoyloxy and in each case A represents lower alkylene, lower alkylidene, lower alkenylen, lower alkenylidene, cycloalkylene, cycloalkylidene or cycloalkyl-lower alkylidene, and $R_3$ represents carboxy, carboxy esterified by a lower alkanol, by a 3- to 8-membered cycloalkanol, by phenol, by a hydroxypyridine, or by a substituted phenol or substituted hydroxypyridine, or represents carbamoyl or carbamoyl mono-substituted by hydroxy, by amino, by phenyl or by substituted phenyl, carbamoyl, mono- or disubstituted by lower alkyl, or carbamoyl di-substituted by 4- to 7-membered alkylene or 3-aza-, 3-lower alkyl-aza-, 3-oxa- or 3-thiaalkylene, wherein a lower alkanol or cycloalkanol can be unsubstituted or substituted by hydroxy, mercapto, optionally substituted phenyl, lower alkoxy, phenyl-lower alkoxy optionally substituted in the phenyl moiety, lower alkylthio, phenyl-lower alkylthio optionally substituted in the phenyl moiety, hydroxy-lower alkoxy, lower alkoxy-lower alkoxy, phenyl-lower alkoxy-lower alkoxy optionally substituted in the phenyl moiety, carboxy-lower alkoxy, lower alkoxycarbonyl-lower alkoxy, by lower alkoxycarbonyl-lower alkoxy containing optionally substituted phenyl or lower alkanoyloxy, and wherein substituted phenyl, phenol or hydroxypyridine can each be substituted by lower alkyl, lower alkoxy, halogen and/or trifluoromethyl, their isomers and their salts, especially pharmceutically acceptable salts, with the proviso that, if A represents methylene or ethylidene and $R_3$ represents ethoxycarbonyl, at least one of the radicals $R_1$ and $R_2$ is different from phenyl, and the further proviso that, if A represents ethylidene and $R_3$ represents carboxy, at least one of the radicals $R_1$ and $R_2$ is different from phenyl, p-methoxyphenyl and p-chlorophenyl.

The invention relates, for example, to compounds of the formula I in which $R_1$ and $R_2$ represent, independently of each other, phenyl and/or phenyl substituted by halogen, hydroxy, lower alkyl, lower alkoxy and/or lower alkanoyloxy, A represents lower alkylene having up to and including 4 carbon atoms, such as methylene, lower alkylidene having up to and including 7 carbon atoms, such as 2,2-propylidene, lower alkenylene having up to and including 4 carbon atoms, such as 1,3-propen-2-ylene, lower alkenylidene having up to and including 7 carbon atoms, such as 1,1-buten-3-ylidene, 3- to 8-membered cycloalkylene, such as cyclopropylene, 3- to 8-membered cycloalkylidene, such as cyclopentylidene, or cycloalkyl-lower alkylidene having up to and including 7 carbon atoms in the alkylidene moiety and having a 3- to 8-membered cycloalkyl moiety, such as 2-cyclohexyl-1,1-ethylidene, and $R_3$ represents carboxy, carboxy esterified by a lower alkanol, a 3- to 8-membered cycloalkanol, phenol or a substituted phenol, or represents carbamoyl, N-mono-, N,N-di-lower alkylcarbamoyl, pyrrolidino-, piperidino, morpholino-, piperazino-, 4-lower alkyl-piperazino-, thiomorpholino- or anilinocarbonyl, or anilinocarbonyl substituted by lower alkyl, lower alkoxy and/or halogen, wherein the lower alkanol or cycloalkanol can be unsubstituted or substituted by hydroxy, mercapto, phenyl, substituted phenyl, lower alkoxy, phenyl-lower alkoxy, phenyl-lower alkoxy substituted in the phenyl moiety, lower alkylthio, phenyl-lower alkylthio, phenyl-lower alkylthio substituted in the phenyl moiety, hydroxy-lower alkoxy, lower alkoxy-lower alkoxy, phenyl-lower alkoxy-lower alkoxy, phenyl-lower alkoxy-lower alkoxy substituted in the phenyl moiety, carboxy-lower alkoxy, lower alkoxycarbonyl-lower alkoxy, by lower alkoxycarbonyl-lower alkoxy containing optionally substituted phenyl, or lower alkanoyloxy, and wherein substituted phenol or phenyl can each be substituted by lower alkyl, lower alkoxy, halogen and/or trifluoromethyl, their isomers and their salts, especially pharmaceutically acceptable salts, with the proviso that, if A represents methylene or ethylidene and $R_3$ represents ethoxycarbonyl, at least one of the radicals $R_1$ and $R_2$ is different from phenyl, and the further proviso that, if A represents ethylidene and $R_3$ represents carboxy, at least one of the radicals $R_1$ and $R_2$ is different from phenyl, p-methoxyphenyl and p-chlorophenyl.

The invention relates, for example, to compounds of the formla I in which one of the radicals $R_1$ and $R_2$ represents pyridyl or 1-oxido-pyridyl, each of which can be unsubstituted or substituted by halogen, hydroxy, lower alkyl, lower alkoxy, and/or lower alkanoyloxy and the other represents phenyl, pyridyl or 1-oxidopyridyl each of which can be unsubstituted or substituted by halogen, hydroxy, lower alkyl, lower alkoxy and/or lower alkanoyloxy, A represents lower alkylene having up to and including 4 carbon atoms, such as methylene, lower alkylidene having up to and including 7 carbon atoms, such as 2,2-propylidene, lower alkenylene having up to and including 4 carbon atoms, such as 1,3-propen-2-ylene, lower alkylidene having up to and including 7 carbon atoms, such as 1,1-buten-3-ylidene, 3- to 8-membered cycloalkylene, such as cyclopropylene, 3- to 8-membered cycloalkylidene, such as cyclopentylidene, or cycloalkyl-lower alkylidene having up to and including 7 carbon atoms in the alkylidene moiety and having a 3- to 8-membered cycloalkyl moiety, such as 2-cylcohexyl-1,1-ethylidene, and $R_3$ represents carboxy, carboxy esterified by a lower alkanol, by a 3- to 8-membered cycloalkanol, by phenol or by a substituted phenol, or represents carbamoyl, N-mono-, N,N-di-lower alkylcarbamoyl, pyrrolidino-, piperidino-, morpholino-, piperazino-, 4-lower alkylpiperazino-, thiomorpholino- or anilinocarbonyl, or anilinocarbonyl substituted by lower alkyl, lower alkoxy and/or halogen, wherein the lower alkanol or cycloalkanol can be unsubstituted or substituted by hydroxy, mercapto, phenyl, substituted phenyl, lower alkoxy, phenyl-lower alkoxy, phenyl-lower alkoxy substituted in the phenyl moiety, lower alkylthio, phenyl-lower alkylthio, phenyl-lower alkylthio substituted in the phenyl moiety, hydroxy-lower alkoxy, lower alkoxy-lower alkoxy, phenyl-lower alkoxy-lower alkoxy, phenyl-lower alkoxy-lower alkoxy substituted in the phenyl moiety, carboxy-lower alkoxy, lower alkoxycarbonyl-lower alkoxy, by lower alkoxycarbonyl-lower alkoxy optionally substituted phenyl, or lower alkanoyloxy, and wherein substituted phenol or phenyl can each be substituted by lower alkyl, lower alkoxy, halogen and/or trifluoromethyl, their isomers and their salts, especially pharmaceutically acceptable salts.

The invention relates, for example, to compounds of the formula I in which $R_1$ and $R_2$ represent, independently of each other, phenyl, and/or phenyl substituted by halogen having an atomic number of up to an including 35, such as chlorine, by hydroxy, by lower alkyl having up to and including 4 carbon atoms, such as methyl, and/or by lower alkoxy having up to and including 4 carbon atoms, such as methoxy, A represents lower alkylene having up to and including 4 carbon atoms, such as methylene, lower alkylidene having up to and including 7 carbon atoms, such as 2,2-propylidene, lower alkenylidene having up to and including 7 carbon atoms, such as 1,1-buten-3-ylidene, or 3- to 8-membered cyclo-lower alkylidene, such as 1,1-cyclopentylidene, and $R_3$ represents carboxy, lower alkoxycarbonyl having up to and including 5 carbon atoms, such as ethoxycarbonyl, carbamoyl, N-mono-lower alkylcarbamoyl having up to and including 4 carbon atoms in the lower alkyl, such as N-methylcarbamoyl, or N,N-di-lower alkylcarbamoyl having up to and including 4 carbon atoms in each lower alkyl, such as N,N-dimethylcarbamoyl, wherein the lower alkoxycarbonyl can be substituted by lower alkanoyloxy having up to and including 5 carbon atoms, such as pivaloyloxy, their isomers and their salts, especially pharmaceutically acceptable salts, with the proviso that, if A represents methylene or ethylidene and $R_3$ represents ethoxycarbonyl, at least one of the radicals $R_1$ and $R_2$ is different from phenyl, and the further proviso that, if A represents ethylidene and $R_3$ represents carboxy, at least one of the radicals $R_1$ and $R_2$ is different from phenyl, p-methoxyphenyl and p-chlorophenyl.

The invention relates, for example, to compounds of the formula I in which one of the radicals $R_1$ and $R_2$ represents phenyl or phenyl substituted by halogen having an atomic number of up to and including 35, such as chlorine, by hydroxy, and/or by lower alkoxy having up to and including 4 carbon atoms, such as methoxy, and the other represents pyridyl, such as 3-pyridyl, or 1-oxidopyridyl, such as 1-oxido-3-pyridyl, each of which can be unsubstituted or substituted by halogen having an atomic number of up to and including 35, such as chlorine, by hydroxy, and/or by lower alkoxy having up to and including 4 carbon atoms, such as methoxy, A represents lower alkylene having up to and including 4 carbon atoms, such as methylene, lower alkylidene having up to and including 7 carbon atoms, such as 2,2-propylidene, lower alkenylidene having up to and including 7 carbon atoms, such as 1,1-buten-3-ylidene, or 3- to 8-membered cyclo-lower alkylidene, such as 1,1-cyclopentylidene, and $R_3$ represents carboxy, lower alkoxycarbonyl having up to and including 5 carbon atoms, such as ethoxycarbonyl, carbamoyl, N-mono-lower alkylcarbamoyl having up to and including 4 carbon atoms in the lower alkyl, such as N-methylcarbamoyl, or N,N-di-lower alkylcarbamoyl having up to and including 4 carbon atoms in each lower alkyl, such as N,N-dimethylcarbamoyl, wherein the lower alkoxycarbonyl can be substituted by lower alkanoyloxy having up to and including 5 carbon atoms, such as pivaloyloxy, their isomers and their salts, especially pharmaceutically acceptable salts.

The invention relates especially to compounds of the formula I in which $R_1$ and $R_2$ represent, independently of each other, phenyl and/or phenyl substituted by lower alkoxy having up to and including 4 carbon atoms, such as methoxy, A represents lower alkylene having up to and including 4 carbon atoms, such as methylene, or especially lower alkylidene having up to and including 4 carbon atoms, such as 2,2-propylidene, and $R_3$ represents carboxy or lower alkoxycarbonyl having up to and including 5 carbon atoms, such as ethoxycarbonyl, their isomers and their salts, especially pharmaceutically acceptable salts, with the proviso that, if A represents methylene or ethylidene and $R_3$ represents ethoxycarbonyl, at least one of the radicals $R_1$ and $R_2$ is different from phenyl, and the further proviso that, if A represents ethylidene and $R_3$ represents carboxy, at least one of the radicals $R_1$ and $R_2$ is different from phenyl and p-methoxyphenyl.

The invention relates more especially to compounds of the formula I in which one of the radicals $R_1$ and $R_2$ represents phenyl or phenyl substituted by halogen having an atomic number of up to and including 35, such as chlorine, by hydroxy or by lower alkoxy having up to and including 4 carbon atoms, such as methoxy, and the other represents pyridyl, such as 3- or 4-pyridyl, or 1-oxidopyridyl, such as 1-oxido-3-pyridyl or 1-oxido-4-pyridyl, A represents lower alkylidene having up to and including 4 carbon atoms, such as 2,2-propylidene, and $R_3$ represents lower alkoxycarbonyl having up to and including 5 carbon atoms, such as ethoxycarbonyl, their isomers and their salts, especially pharmaceutically acceptable salts.

The invention relates more especially to compounds of the formula I in which one of the radicals $R_1$ and $R_2$ represents phenyl or phenyl substituted by halogen having an atomic number of up to and including 35, such as chlorine, by hydroxy or by lower alkoxy having up to and including 4 carbon atoms, such as methoxy, and the other represents pyridyl, such as 3- or 4-pyridyl, or 1-oxidopyridyl, such as 1-oxido-3-pyridyl or 1-oxido-4-pyridyl, A represents lower alkylidene having up to and including 4 carbon atoms and containing a quaternary carbon atom, such as 2,2-propylidene, wherein the quaternary carbon atom is bonded directly to the imidazole ring, and $R_3$ represents lower alkoxycarbonyl having up to and including 5 carbon atoms, such as ethoxycarbonyl, their isomers and their salts, especially pharmaceutically acceptable salts.

The invention relates most especially to compounds of the formula I in which one of the radicals $R_1$ and $R_2$ represents phenyl and the other represents 1-oxidopyridyl, such as 1-oxido-3-pyridyl, A represents 2,2-propylidene and $R_3$ represents lower alkoxycarbonyl having up to and including 5 carbon atoms, such as ethoxycarbonyl, their isomers and their salts, especially pharmaceutically acceptable salts.

The invention relates in particular to the compounds mentioned in the Examples and their salts, especially pharmaceutically acceptable salts of such compounds having salt-forming groups, and to the manufacturing processes mentioned in the Examples.

The invention relates in particular to the compounds of the formula I mentioned in the Examples and their salts, especially pharmaceutically acceptable salts of such compounds having salt-forming groups.

The novel compounds of the formula I or the salts thereof can be manufactured in a manner known per se.

One method comprises, for example, splitting off H—Z, while introducing an optional additional bond, from a compound of the formula

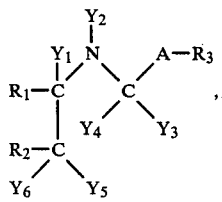
(II)

in which one of the radicals $Y_1$ and $Y_6$ represents hydroxy or amino, and the other radical and $Y_2$ each represents hydrogen, and $Y_3$ together with $Y_4$ and $Y_5$ represents a group of the formula =N—, or in which $Y_1$ together with $Y_6$ represents a bond, $Y_2$ is hydrogen, $Y_3$ represents hydroxy or amino, and $Y_4$ together with $Y_5$ represents a group of the formula —NH—, or in which $Y_1$ together with $Y_6$ represents a bond, $Y_2$ together with $Y_3$ represents an additional bond and one of the radicals $Y_4$ and $Y_5$ represents amino and the other represents amino, hydroxy or reactive esterified hydroxy, especially halogen or sulphonyloxy, or in which $Y_1$ is hydroxy, $Y_2$ and $Y_3$ each represents hydrogen, $Y_4$ represents hydroxy or amino and $Y_5$ together with $Y_6$ represents a group of the formula =NH or, if $Y_4$ is amino, represents oxo or imino, or from a tautomer and/or a salt thereof, and, if desired, converting the free compound obtainable in accordance with the process into a salt or converting a salt obtainable in accordance with the process into the free compound or into a different salt and/or, if desired, separating a mixture of isomeric compounds of the formula I obtainable in accordance with the invention into the individual isomers.

Z represents hydroxy or amino $Y_1$ or $Y_6$, $Y_3$ or $Y_4$ or $Y_5$ respectively, or halogen or sulphonyloxy $Y_4$ or $Y_5$ respectively.

Reactive esterified hydroxy is, for example, hydroxy esterified by an inorganic mineral acid, such as a hydrohalic acid, or by an organic sulphonic acid, such as a lower alkanesulphonic acid or optionally substituted benzenesulphonic acid and represents especially halogen, for example chlorine or bromine, or sulphonyloxy, for example methane- or p-toluenesulphonyloxy.

Tautomers of compounds of the formula II are, for example, those in which a partial enol or enamine grouping of the formula

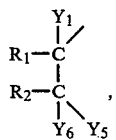
(IIa)

in which $Y_1$ together with $Y_6$ represents an additional bond and $Y_5$ represents hydroxy or amino, is present respectively in the corresponding tautomeric keto or ketimine form in which $Y_1$ is hydrogen and $Y_5$ together with $Y_6$ represents oxo or imino, respectively, and/or those in which a partial enol or enamine grouping of the formula

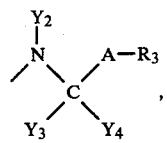
(IIb)

in which $Y_2$ together with $Y_3$ represents a bond and $Y_4$ represents hydroxy or amino, is present in the corresponding tautomeric form in which $Y_2$ is hydrogen and $Y_3$ together with $Y_4$ represents oxo or imino, respectively, the mentioned tautomers being in equilibrium with each other.

The splitting off of H—Z from a compound of the formula II, a tautomer and/or a salt thereof is carried out in customary manner, especially in the manner known from the literature for analogous reactions, if necessary while heating, such as within a temperature range of from approximately 20° to approximately 250° C., under pressure and/or in the presence of a catalytic agent, preferably an acid. Suitable acids are, for example, inorganic acids, such as mineral acids, for example sulphuric acid, polyphosphoric acid or a hydrohalic acid, such as hydrochloric acid, or organic acids, such as lower alkanecarboxylic acids, for example acetic acid. The reaction is carried out, if necessary, in an inert solvent, for example an optionally halogenated hydrocarbon, such as chloroform, chlorobenzene, hexane or toluene, a lower alkanol, such as methanol or ethanol, a carboxylic acid amide, such as a lower alkane-carboxylic acid amide, for example dimethylformamide or formamide, or a lower alkanecarboxylic acid, such as formic or acetic acid, and/or under an inert gas, such as nitrogen.

The starting materials of the formula II, their tautomers and/or salts are predominantly formed in situ and further reacted, under the reacted conditions and without isolation, to form the compound of the formula I according to processes known per se. The splitting off of H—Z can take place with direct cyclisation or following prior cyclisation.

Thus, in a preferred form of the above-mentioned process, for example a diketone of the formula

(IIIa)

can be reacted with an aldehyde of the formula $R_3$—A—C(=O)—H (IIIb) or a salt thereof, with an excess of ammonia and while heating. In this process, there is formed, for example, as an intermediate, a compound of the formula II, for example one in which $Y_1$ represents hydroxy, and $Y_2$ and $Y_6$ each represents hydrogen and $Y_3$ together with $Y_4$ and $Y_5$ represents a group of the formula =N—, for example

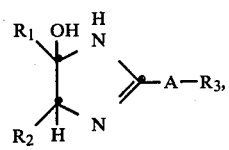

or a tautomeric form thereof, that further reacts according to the invention under the reaction conditions.

Furthermore, in further preferred forms of the above-described process, an acylated α-amino-ketone of the formula

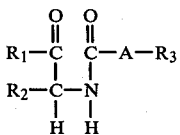 (IIIc)

or a salt thereof can be reacted with ammonia. This reaction is carried out, for example, while heating, for example within a temperature range of from approximately 50° to approximately 250° C., and under inert conditions.

The starting materials of the formula (IIIa) are known or are manufactured according to processes known per se. For example, a compound of the formula

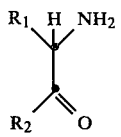 (IIIh)

or a salt thereof is used as starting material and is reacted with an acid derivative of the formula $R_3$—A—COOH (IIIi), for example a corresponding anhydride, such as a carbonyl halide compound.

In a further, especially preferred variant of the process described at the beginning, a compound of the formula

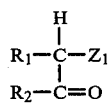 (IIId)

in which $Z_1$ represents reactive esterified hydroxy, or a salt thereof is reacted with a compound of the formula $R_3$—A—$Z_2$ (IIIe), in which $Z_2$ represents an amidino radical or ammonium carboxylate, or a salt thereof optionally with ammonia.

The reaction with an amidine of the formula (IIIe) is usually carried out while heating, for example within a temperature range of from approximately 50° to approximately 250° C.

The reaction of the ammonium carboxylate of the formula (IIIe) with a compound of the formula (IIId) is carried out with an at least 3-molar or, if the compound of the formula (IIId) is in salt form, at least 4-molar, excess of the ammonium salt of the compound of the formula (IIIe), optionally while heating, for example within a temperature range of from approximately 50° to approximately 250° C., preferably at from 90° to 120° C., it being possible for the compound of the formula (IIIe) to serve simultaneously as solvent. This variant can also be modified, for example, by using the ammonium salt of the formula III in an approximately equimolar quantity with respect to the reactive ester $Z_1$ and, in addition, adding ammonia, optionally in the form of a salt of an acid that is weaker than $R_3$—COOH, in excess, preferably in a 3- to 5-fold excess.

A reactive esterified hydroxy group $Z_1$ is, for example, a hydroxy group esterified preferably by strong inorganic or organic acids, such as strong mineral acids, for example hydrohalic acids, such as hydrochloric acid or hydrobromic acid, or strong organic sulphonic acids, such as corresponding lower alkane- or arylsulphonic acids, for example methanesulphonic acid or an optionally substituted benzenesulphonic acid, and is, for example, halogen, such as chlorine or bromine, lower alkylsulphonyloxy, for example methyl- or ethylsulphonyloxy, or arylsulphonyloxy, for example p-toluene- or benzenesulphonyloxy.

The ammonium salt of the formula (IIIe) can also be formed in situ under the reaction conditions, for example by commencing with the free acid of the formula (IIIe) in the reaction mixture and adding liquid or gaseous ammonia. In this form of the process, the ammonia can also be added in the form of a salt with an acid that is weaker than $R_3$—COOH, such as carbonic acid.

Suitable solvents are, for example, optionally halogenated hydrocarbons, such as optionally halogenated aliphatic, cycloaliphatic or aromatic hydrocarbons, such as hexane, cyclohexane, toluene, chloroform, or chlorobenzene, alkanols, such as propanol, isopropanol, butanols, pentanols or octanols, ethers, such as dimethoxyethane, ethylene glycol monoethyl ether, dioxan or tetrahydrofuran, lower alkanecarboxylic acids, such as formic or acetic acid or preferably acids of the formula (IIIh), amides, such as lower alkanecarboxylic acid amides, for example formamide or dimethylformamide, and lactams, for example N-methylpyrrolidone, sulphoxides, such as dimethyl sulphoxide, or water.

A preferred form of this variant for the preparation, according to the invention, of compounds of the formula I via compounds of the formula II is to react a compound of the formula (IIId), in which $Z_1$ represents, for example, halogen, such as bromine, with an ammonium salt of the formula (IIIe) at a reaction temperature of approximately 100° C. The compound of the formula (IIIe) is added in excess, for example in a ratio to the ester of the formula (IIId) of approximately 4:1 to approximately 6:1, and can be formed in situ, for example by reacting the corresponding acid under the reaction conditions with liquid ammonia.

The starting materials of the formula (IIId) are known or can be manufactured according to processes known per se.

They can be obtained, for example, by ester condensation of esterified acids of the formulae $R_1$—CH$_2$—COOH and $R_2$—CH$_2$—COOH with esterified acids of the formulae $R_1$—COOH and $R_2$—COOH, respectively, preferably in the presence of a base. The resulting α-methylene ketone of the formula

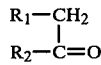

is, for example, brominated and thus converted into a compound of the formula (IIId) in which $Z_1$ represents bromine.

In addition, in a further preferred form of the process, an oxazole of the formula

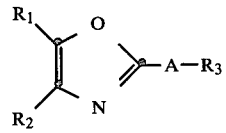 (IIIf)

can be reacted with ammonia via compounds of the formula II to form compounds of the formula I in which R₃ represents carbamoyl.

This reaction is carried out optionally under pressure, for example at 185 atmospheres gauge, and/or while heating, for example to from approximately 100° to approximately 250° C.

The compounds of the formula (IIIf) can, for their part, be manufactured according to processes known per se, for example by reacting compounds of the formula

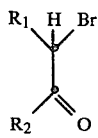 (IIIg)

with carboxylic acids of the formula R₃—A—COOH or the salts thereof, and with ammonia.

In this case, one compound of the formula II, in each case, is formed which, according to the invention, reacts further, especially in situ, to form a compound of the formula I.

Some of the process variants described above can be so carried out by using mild conditions that the compounds of the formula II or their tautomers and/or salts can be isolated.

Compounds of the formula I or salts thereof can also be manufactured, for example, by reducing a compound of the formula

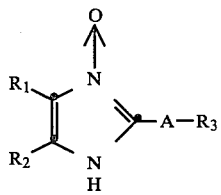 (IV)

or a salt thereof to a compound of the formula I and, if desired, converting the free compound obtainable in accordance with the process into a salt or a salt obtainable in accordance with the process into the free compound of into a different salt.

The reduction is carried out according to processes known per se. Thus, compounds of the formula (IV) or salts thereof are treated with hydrogen in the presence of a hydrogenation catalyst or with a dithionite, for example sodium dithionite, or with a phosphorus halide, for example phosphorus trichloride. As hydrogenation catalysts there can be used, for example, elements of sub-group VIII and derivatives thereof, such as platinum, palladium or palladium chloride, which may be applied to a customary carrier, such as active carbon or alkaline earth metal compounds, for example barium carbonate, or Raney nickel.

The reduction can be carried out, if necessary, while cooling or heating, for example within a temperature range of from approximately 0° to approximately 150° C., in an inert solvent, such as a halogenated hydrocarbon, for example chloroform, carbon tetrachloride or chlorobenzene, or an ether, such as dimethoxyethane, diethyl ether, dioxan or tetrahydrofuran, and/or under an inert gas, for example nitrogen.

The starting materials of the formula IV or salts thereof can be obtained in a manner known per se, for example by reacting a compound of the formula

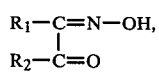 (IVa)

a tautomer or a salt thereof in situ with an excess of ammonia and an aldehyde of the formula R₃—A—C(=O)—H, (IIIb) at elevated temperature.

Compounds of the formula I can also be manufactured by converting the radical R₃' into a radical R₃ in a compound of the formula

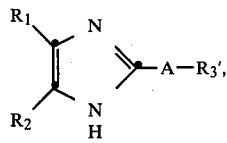 (V)

in which R₃' represents a radical that can be converted into R₃, and, if desired, converting the free compound obtainable in accordance with the process into a salt or a salt obtainable in accordance with the process into the free compound or into a different salt.

Such groups R₃' are, for example, functionally modified carboxy groupings other than optionally esterified or amidated carboxy, such as cyano or ortho-ester groupings, which can be converted into a radical R₃, for example, by solvolysis, for example hydrolysis or alcoholysis.

There come into consideration as ortho-ester groupings: ortho-ester groups etherified by a lower alkanol or esterified by a mineral acid, such as tri-lower alkoxy-, tri-halo- or lower alkoxy di-halomethyl, especially triethoxy- or trichloromethyl.

The solvolysis is carried out in customary manner, if necessary in the presence of a base, such as an alkali metal hydroxide, for example sodium or potassium hydroxide, or a proton acid, for example a mineral acid, such as sulphuric acid or a hydrohalic acid, for example hydrochloric acid, or, for example, an organic carboxylic or sulphonic acid, such as acetic acid or p-toluenesulphonic acid. The solvolysis is carried out, if necessary, in an inert solvent, such as in a lower alkanol, for example methanol or ethanol, a ketone, such as acetone, or an ether, such as dioxan, and, if necessary, while cooling or heating, for example at from approximately 0° to approximately 150° C. In this manner, cyano, optionally substituted carbamoyl or an ortho-acid grouping R₃' can be converted by hydrolysis into free carboxy, by alcoholysis into esterified carboxy or by ammonolysis or aminolysis into carbamoyl or N-substituted carbamoyl, respectively.

Further groups that can be converted into carboxy or esterified carboxy R₃ are, for example, radicals that can be converted into these by oxidation, such as optionally esterified or etherified hydroxymethyl or optionally acetalised formyl.

Esterified hydroxymethyl is, for example, hydroxymethyl esterified by a mineral acid, such as a hydrohalic acid, such as hydrochloric acid, or a carboxylic acid, such as a lower alkanecarboxylic acid, for example acetic acid, or an optionally substituted benzoic acid. Acetalised formyl is, for example, formyl acetalised by a lower alkanol or a lower alkanediol, such as dimethoxy-, diethoxy- or ethylenedioxyformyl.

The oxidation of such groups $R_3'$ is carried out in a manner known per se, for example by reaction in a suitable oxidising agent, for example in an inert solvent, such as a lower alkanecarboxylic acid, for example acetic acid, a ketone, for example acetone, an ether, for example tetrahydrofuran, a heterocyclic aromatic compound, for example pyridine, or water or a mixture thereof, if necessary while cooling or heating, for example from approximately 0° to approximately 150° C. As oxidising agents there come into consideration, for example, oxidising transition metal compounds, especially those with elements of sub-groups I, VI, VII or VIII. There may be mentioned as examples: silver compounds, such as silver nitrate, oxide or picolinate, chromium compounds, such as chromium trioxide or potassium dichromate, manganese compounds, such as potassium ferrate, tetrabutylammonium or benzyl(triethyl)ammonium permanganate. Further oxidising agents are, for example, suitable compounds with elements of main group 4, such as lead dioxide, or halogen-oxygen compounds such as sodium iodate or potassium periodate.

Thus, for example, hydroxymethyl and optionally acetalised formyl is oxidised to carboxy $R_3$, whereas the oxidation of etherified hydroxymethyl R results in esterified carboxy $R_3$.

The starting materials of the formula V are manufactured according to processes known per se. For example, a diketone of the formula

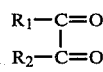

(IIIa)

is used as starting material and is reacted with ammonia and an aldehyde of the formula $R_3'$—A—C(=O)—H in an inert solvent and while heating and the compound of the formula V formed in situ is further reacted without isolation.

A further method of manufacturing compounds of the formula I or salts thereof, which is known per se, comprises, for example, converting $R_4$ into hydrogen in a compound of the formula

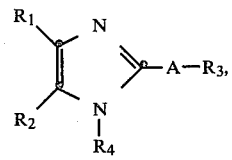

(VI)

in which $R_4$ represents a group that can be converted into hydrogen, or in a salt thereof, and, if desired, converting the free compound obtainable in accordance with the process into a salt or a salt obtainable in accordance with the process into the free compound or into a different salt.

A radical $R_4$ that can be converted into hydrogen is, for example, one of the customary suitable amino-protecting groups. From among the number of suitable groups that can be converted into hydrogen, there may be mentioned, for example, optionally cyclic alkyl radicals interrupted by oxygen, or optionally substituted aralkyl, sulphenyl or acyl radicals. As alkyl radicals interrupted by oxygen there come into consideration, for example, lower alkoxy-lower alkyl, such as ethoxyethyl, phenyl-lower alkoxy-lower alkyl, such as benzyl methyl ether, tetrahydrofuranyl or tetrahydropyranyl. Optionally substituted aralkyl radicals are, for example, those which have, in the aryl moiety, for example phenyl, biphenyl, anthryl and/or pyridyl and, in the alkyl moiety, lower alkyl, such as methyl or isopropyl, such as benzyl substituted in the phenyl moiety by lower alkyl, lower alkoxy or halogen, such as 3,5-dimethoxy-, 2,4,6-trimethoxy- or 4-bromobenzyl, 2-diphenyl-2-propyl, di- or tri-arylmethyl, such as diphenyl-, triphenyl- or $\alpha,\alpha$-diphenyl-4-pyridylmethyl. Sulphenyl radicals are, for example, phenylsulphenyl radicals optionally substituted by nitro, such as 3-nitrophenyl-sulphenyl. By acyl radicals there are to be understood, for example, those which are derived from aromatic carboxylic acids or alkanecarboxylic acids and from sulphonic acids, such as optionally sustituted benzyloxycarbonyl, lower alkanoyloxycarbonyl, for example tert.-butoxycarbonyl, alkanoyl, such as acetyl, or sulphonyl, such as p-toluenesulphonyl.

The splitting off of the amino-protecting group $R_4$ is effected by methods known per se. It can be effected, for example, by reduction, for example by hydrogenolysis with hydrogen or nascent hydrogen, or by acidolysis, for example with mineral acids, such as hydrohalic acids, such as hydrochloric or hydrobromic acid, or with optionally substituted lower alkanecarboxylic acids, such as acetic acid or trifluoroacetic acid, if necessary while cooling or heating, for example within a temperature range of from approximately 0° to approximately 150° C., and in an inert solvent. Inert solvents are, for example, amides, such as dimethylformamide, halogenated hydrocarbons, such as chloroform or carbon tetrachloride, lower alkanols, such as methanol or ethanol, ketones, such as di-lower alkyl ketones, for example acetone, ethers, such as tetrahydrofuran, or nitriles, such as acetonitrile. The conversion of benzyl $R_4$ into hydrogen is carried out especially by means of hydrogen in acetic acid and in the presence of a hydrogenation catalyst, such as palladium-carbon, with sodium in liquid ammonia, with hydrobromic acid in acetic acid or with hydrogen fluoride, and of triphenylmethyl $R_4$ with hydrochloric acid in acetonitrile, with trifluoroacetic acid in acetic acid or with acetic acid, or of tert.-butyl $R_4$ with trifluoroacetic acid.

The starting materials of the formula (VI) are manufactured according to processes known per se, for example starting from compounds of the formula

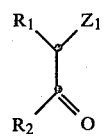

(VIa)

or salts thereof, in which $Z_1$ represents reactive etherified hydroxy, such as halogen, and reacting these with an ammonium salt of the acid $R_3'$—A—COOH (VIb) in which $R_3'$ represents optionally etherified hydroxymethyl, and ammonia. In the resulting compound of the formula

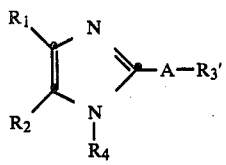

$R_3'$ is converted into $R_3$. The conversion is carried out by oxidation, hydroxymethyl and lower alkoxymethyl $R_3'$ being oxidised to form carboxy and lower alkoxycarbonyl $R_3$, respectively. Ammonolysis or aminolysis can, if desired, follow in a further reaction step.

In a further method, compounds of the formula I are obtained by reacting compounds of the formula

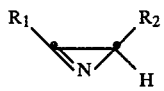

or tautomers thereof with compounds of the formula $R_3$—A—CN (VIIb) and, if desired, converting free compounds obtainable in accordance with the process into salts or salts obtainable in accordance with the process into the free compounds or different salts.

The reaction is carried out in a manner known per se, for example in the presence of a Lewis acid. The reaction is carried out, if necessary, in an inert solvent, under an inert gas, for example nitrogen, and/or within a temperature range of from approximately −50° to approximately +100° C., especially between −10° and approximately +30° C. Advantageously, compounds of the formula VIIb are used, in addition, as solvents.

As Lewis acids, i.e. electron-acceptors, there are used, for example, compounds of elements of main groups 3 and 5 and of sub-groups II and VIII of the periodic system. There come into consideration, especially, halides of boron, aluminium, tin, antimony and iron, especially boron tirfluoride etherate, and also aluminium chloride, tin(IV) chloride, zinc chloride and iron chloride.

Inert solvents are, for example, hydrocarbons optionally containing nitro, such as nitroaromatic compounds, for example nitrobenzene.

The formation of compounds of the formula I using starting materials of the formulae VIIa and VIIb takes place under the reaction conditions, predominantly in situ and without isolation of possible intermediate steps. The reaction can, of course, also be carried out using, as starting material, stable vinylnitrenium compounds of the formula

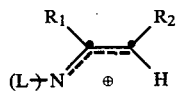

in which optionally present L represents a Lewis acid bonded in the manner of a complex.

The formation of vinylnitrenium compounds of the formula VIIc is induced by supplying energy, for example by thermolysis or photolysis, or by the Lewis acids mentioned above.

The starting materials of the formulae VIIa, VIIb and VIIc are, for example, known or are manufactured according to methods known per se.

In the above-described processes for the manufacture of compounds of the formulae II, IV, Va and Vb, the ammonia, which is predominantly added in excess, can also be used in the form of an agent that gives up ammonia, liberation taking place at elevated temperature and optionally under pressure. As agents that give up ammonia there come into consideration, for example, ammonium salts of lower alkanecarboxylic acids, preferably ammonium acetate, or of a carboxylic acid of the formula $R_3$—A—COOH, also a suitable lower alkanecarboxylic acid amide, especially formamide.

The compounds of the formula I can also be manufactured by dehydrogenating a compound of the formula

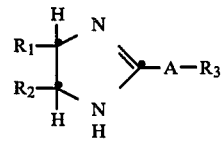

or an isomer thereof, to form compounds of the formula I and, if desired, converting the free compound obtainable in accordance with the process into a salt, or a salt obtainable in accordance with the process into the free compound or into a different salt.

Compounds of the formula VIII can be present, for example, in the form of an individual stereoisomer, an optical isomer, such as an enantiomer, or as mixtures of the same, such as racemates, and also as geometrical (cis-trans) isomers.

Dehydrogenation of compounds of the formula VIII is carried out in a manner known per se, especially at elevated temperature, for example within a temperature range of from approximately 100° to approximately 300°, optionally using a dehydrogenating agent. As such agents, there come into consideration, for example, dehydrogenation catalysts, for example elements of sub-groups, preferably of sub-group VIII, such as palladium or platinum, or salts thereof, such as rutheniumtriphenyl phosphide chloride, the catalysts optionally being applied to a suitable carrier, such as carbon, aluminium oxide or silicon dioxide. Further dehydrogenating agents are, for example, quinones, such as p-benzoquinones, for example tetrachloro-p-benzoquinone or 2,3-dichloro-5,6-dicyano-p-benzoquinone, or such as anthraquinones, for example phenanthren-9,10-quinone; N-halosuccinimides, such as N-chlorosuccinimide, or manganates, such as barium manganate. The reaction is carried out in an inert, optionally high-boiling, solvent, such as an ether, for example diphenyl ether, if necessary under pressure, in a closed vessel and/or under an inert gas, for example nitrogen.

The compounds of the formula VIII to be used as starting materials can be manufactured, for example, by reacting a compound of the formula

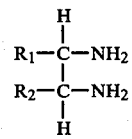

or a salt thereof, with compounds of the formula $R_3$—A—$Z_3$ (VIIIb) in which $Z_3$ represents optionally functionally modified carboxy. Functionally modified carboxy is, inter alia, esterified carboxy, such as lower alkoxycarbonyl, amidated carboxy, such as optionally substituted carbamoyl, or anhydridised carboxy, such as carbonyl halide.

In a preferred variant of the above process, the compounds of the formula I are obtained under the reaction conditions in situ, starting from compounds of the formulae VIIIa and VIIIb, without isolating compounds of the formula VIII, for example by heating compounds of the formulae VIIIa and VIIIb in nitrobenzene.

The aldehyde of the formula R₃—A—C(=O)—H (IIIb) can also be liberated in the above-described processes for manufacturing compounds of the formulae II, IV and V, for example also under the reaction conditions, from an oxazine derivative of the formula

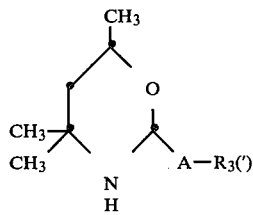 (IX)

The compounds of the formula IX can be manufactured, for example, by reacting 2-methyl-2,4-pentanediol with a nitrile of the formula R₃(')—A—CN in the presence of sulphuric acid. The correspondingly substituted dihydro-1,3-oxazine formed during the reaction is reduced in a mixture of tetrahydrofuran and ethanol at −45° C. and a pH of approximately 7 under the action of sodium borohydride to form tetrahydro-1,3-oxazine of the formula IX.

A compound obtainable according to the invention can be converted in customary manner into a different compound of the formula I.

Thus, in compounds of the formula I obtainable according to the invention free and esterified carboxy groups R₃ can each be converted into the other.

A free carboxyl group R₃ can be esterified to form an esterified carboxyl group R₃, for example in customary manner, for example by treating with a diazo-lower alkane, di-lower alkylformamide acetal, alkyl halide or tri-lower alkyloxonium, tri-lower alkylcarboxonium or di-lower alkylcarbonium salts, such as hexachloroantimonate or hexafluorophosphate, or especially by reacting with the corresponding alcohol or a reactive derivative, such as a carboxylic acid ester, phosphorous acid ester, sulphurous acid ester or carbonic acid ester, for example a lower alkanecarboxylic acid ester, tri-lower alkyl phosphite, di-lower alkyl sulphite or the pyrocarbonate, or a mineral acid ester or sulphonic acid ester, for example the hydrochloric or hydrobromic acid ester, or sulphuric acid ester, benzenesulphonic acid ester, toluenesulphonic acid ester or methanesulphonic acid ester, of the corresponding alcohol of an olefin derived therefrom.

The reaction with the corresponding alcohol itself can advantageously be effected in the presence of an acid catalyst, such as a proton acid, for example hydrochloric or hydrobromic acid, sulphuric acid, phosphoric acid, boric acid, benzenesulphonic acid and/or toluenesulphonic acid, or a Lewis acid, for example boron trifluoride etherate, in an inert solvent, especially an excess of the alcohol used and, if necessary, in the presence of a water-bining agent and/or while removing the water of reaction by distillation, for example azeotropically, and/or at elevated temperature.

The reaction with a reactive derivative of the corresponding alcohol can be carried out in customary manner, starting from a carboxylic, phosphorous, sulphurous or carbonic acid ester, for example in the presence of an acid catalyst, such as one of those mentioned above, in an inert solvent, such as an aromatic hydrocarbon, for example in benzene or toluene, or an excess of the alcohol derivative used or of the corresponding alcohol. Starting from a mineral acid ester or sulphonic acid ester, the acid to be esterified is reacted advantageously in the form of a salt, for example the sodium or potassium salt, and the operation is carried out, if necessary, in the presence of a basic condensation agent, such as an inorganic base, for example sodium, potassium or calcium hydroxide or carbonate, or a tertiary organic nitrogen base, for example triethylamine or pyridine, and/or in an inert solvent, such as one of the tertiary nitrogen bases mentioned above or a polar solvent, for example in dimethylformamide, and/or at elevated temperature.

The reaction with a di-lower alkylformamide acetal, such as dimethylformamide acetal, is effected optionally while heating, whilst the reaction with an alkyl halide is carried out in the presence of a base, such as an amine, for example triethylamine.

The reaction with an olefin can be effected, for example, in the presence of an acid catalyst, for example a Lewis acid, such as boron trifluoride, a sulphonic acid, for example p-toluenesulphonic acid, or, especially, a basic catalyst, for example sodium or potassium hydroxide, advantageously in an inert solvent, such as an ether, for example diethyl ether or tetrahydrofuran.

The above-described conversions of free into esterified carboxyl groups R₃ can, however, alternatively be carried out in such a manner that a compound of the formula I in which R₃ is carboxyl is first converted, in customary manner, into a reactive derivative, for example converted by means of a halide of phosphorus or sulphur, for example by means of phosphorus trichloride or bromide, phosphorus pentachloride or thionyl chloride, into an acid halide, or converted by reaction with a corresponding alcohol into a reactive ester, i.e. an ester having electron-attracting structures, such as the ester with phenol, thiophenol, p-nitrophenol or cyanomethyl alcohol, and the resulting reactive derivative is then reacted, in customary manner, for example as described hereinafter for the transesterification or interchange of esterified carboxyl groups R₃, with a corresponding alcohol to form the desired group R₃.

An esterified carboxyl group R₃ can be converted into the free carboxyl group R₃ in customary manner, for example by hydrolysis in the presence of a catalyst, for example a basic or acidic agent, such as a strong base, for example sodium or potassium hydroxide, or a mineral acid, for example hydrochloric acid, sulphuric acid or phosphoric acid.

An esterified carboxyl group R₃ can also be transesterified to a different esterified carboxyl group R₃ in customary manner, for example by reaction with a metal salt, such as the sodium or potassium salt, of a corresponding alcohol or with the latter itself, in the presence of a catalyst, for example a strong base, for example sodium or potassium hydroxide, or a strong acid, such as a mineral acid, for example hydrochloric acid, sulphuric acid or phosphoric acid, aor an organic sulphonic acid, for example p-toluenesulphonic acid, or a Lewis acid, for example boron trifluoride etherate.

Furthermore, free carboxy and reactively functional carboxy derivatives can be converted into a desired amidated form by solvolysis with ammonia or a primary or secondary amine, it being possible to use also hydroxylamines and hydrazines, in customary manner while dehydrating, optionally in the presence of a condensation agent. The condensation agents used are preferably bases, for example inorganic bases, such as alkali metal hydroxides, for example sodium or potassium hydroxide, organic nitrogen bases, such as tertiary amines, for example pyridine, tributylamine or N-dimethylaniline, or tetrahalosilanes, such as tetrachlorosilane. Similarly, in compounds of the formula I obtainable according to the invention, in which $R_3$ represents amidated carboxy, the amide bond can be split according to methods known per se, thereby converting the carbamoyl into free carboxy. For this purpose, the operation is carried out in the presence of a catalyst, for example a base, such as an alkali metal or alkaline earth metal hydroxide or carbonate, for example sodium, potassium or calcium hydroxide or carbonate, or an acid, such as a mineral acid, for example hydrochloric acid, sulphuric acid or phosphoric acid.

If at least one of the substituents $R_1$, $R_2$ and $R_3$ contains, as additional substituent, hydroxy, the latter can be etherified in a manner known per se. The reaction with an alcohol component, for example with a lower alkanol, such as ehtanol, in the presence of acids, for example a mineral acid, such as sulphuric acid, or of dehydrating agents, such as dicyclohexyl carbodiimide, results in lower alkoxy. Phenols and salts thereof can be converted into corresponding lower alkylphenyl ethers and arylphenyl ethers, for example in the presence of bases, such as alkali metal hydroxides or carbonates, for example sodium hydroxide or potassium carbonate, with the aid of di-lower alkyl sulphates, diazo-lower alkanes or alkyl and arylhalides, respectively. Conversely, ethers can be split to form alcohols. Thus, for example, aromatic alcohols are produced from aryloxyaryl compounds by splitting the ethers by means of acids, such as mineral acids, for example hydrohalic acids, such as hydrobromic acid, or such as Lewis acids, for example halides of elements of the main group 3, such as boron tribromide, or by means of bases, for example lower alkylamines, such as methylamine.

Furthermore, hydroxy can be converted into lower alkanoyloxy, for example by reaction with a desired lower alkanecarboxylic acid, such as acetic acid or a reactive derivative thereof, for example in the presence of an acid, such as a proton acid, for example hydrochloric acid, hydrobromic acid, sulphuric acid, phosphoric acid or a benzenesulphonic acid, in the presence of a Lewis acid, for example boron trifluoride etherate, or in the presence of a water-binding agent. Conversely, esterified hydroxy can be solvolysed to hydroxy, for example by base catalysis.

Resulting free compounds of the formula I can be converted into salts in a manner known per se. Groups $R_1$ or $R_2$ having hydroxy, and carboxy $R_3'$ are converted with corresponding bases, such as alkali metal hydroxides, into the salts with bases mentioned at the beginning or, by treatment with an acid that forms acid addition salts, such as those acids indicated above, into acid addition salts.

Resulting salts can be converted in a manner known per se into the free compounds, for example by treatment with an acidic reagent, such as a mineral acid, or a base, for example an alkali hydroxide.

Owing to the close relationship between the novel compound in the free form and in the form of its salts, hereinbefore and hereinafter the free compound and its salts shall be understood to mean optionally also the corresponding salts and the free compound, respectively, where appropriate with regard to meaning and purpose.

Depending on the starting materials and procedures chosen, the novel compound can be in the form of one of the possible isomers or as a mixture of the same.

The novel compound including its salts can also be obtained in the form of its hydrates or include other solvents used for crystallisation.

Depending on the starting materials and procedures chosen, the novel compounds can be obtained in the form of one of the possible isomers or as mixtures of the same, for example depending on the number of asymmetric carbon atoms, as pure optical isomers, such as antipodes, or as isomeric mixtures, such as racemates, diastereoisomeric mixtures or racemic mixtures, and also as tautomers.

Resulting diastereoisomeric mixtures and racemic mixtures can be separated, in known manner, on the basis of the physico-chemical differences between the constituents, into the pure isomers, diastereoisomers or racemates, for example by chromatography and/or fractional crystallisation. Resulting racemates can also be resolved according to known methods into the optical antipodes, for example by recrystallisation from an optically active solvent, by means of microorganisms or by reaction of an acidic end product with an optically active base that forms salts with the racemic acid and separation of the salts obtained in that manner, for example on the basis of their differing solubility, into the diastereoisomers from which the antipodes can be freed by the action of suitable agents. Advantageously, the more active of the two antipodes is isolated.

The invention relates also to those forms of the process according to which compounds obtainable as intermediates at any stage of the process are used as starting material and the remaining steps are carried out or a starting material is used in the form of a salt or, especially, is formed under the reaction conditions.

The invention relates also to the starting materials of the formulae II, IIIa, IIIb, IIIc, IIId, IIIe, IIIf, IV, V, VI, VIIa and VIII that have been developed specifically for the manufacture of the compounds according to the invention, the processes for their manufacture and their use.

The starting materials of the formulae II, IIIa, IIIb, IIIc, IIId, IIIe, IIIf, IV, V, VI, VIII and VIIa, which have been specially developed for the production of the compounds of the invention, the processes for obtaining them and the use thereof, likewise constitute objects of the invention.

Thus, for example, compounds of the formula IIIf, wherein one $R_1$ and $R_2$ is heteroaryl and the other is carbocyclic aryl or heteroaryl, and A is a divalent hydrocarbon radical, and $R_3$ is carboxyl or amidated carboxyl, the isomers and salts thereof, with the proviso that $R_1$ and $R_2$ are different form naphthyl, thienyl or furyl, exhibit a pronounced anti-inflammatory action, especially when applied topically. This action can be determined e.g. from the inhibitory effect on ear edema induced in normal rats by croton oil in the dosage range from about 1 to 100 mg/ml [method of G. Tonelli and L. Thibault, Endocinology 77, 625 (1965)]. Accordingly, corresponding compounds of the formula IIIf can be used as medicaments, in particular as antiphlogistic agents for the external (topical) treatment of inflammatory dermatoses.

The corresponding compounds of the formula IIIf, processes for obtaining them, pharmaceutical preparations containing them, and their use e.g. as medicinal compounds, likewise constitute objects of the invention.

The pharmaceutical preparations according to the invention, which contain the compound according to the invention or pharmaceutically acceptable salts thereof, are preferably those suitable for topical administration, and also for enteral administration, such as oral or rectal administration, and parenteral administration to (a) warmblooded animal(s), the pharmacological active substance being present therein on its own or together with a pharmaceutically acceptable carrier. The daily dosage of the active substance depends on age and individual condition and also on the mode of administration. Appropriate agents having a concentration range of from approximately 1 to approximately 10% W/W, for example in the form of creams, ointments or solutions, can be administered, for example, 2 or 3 times daily.

As pharmaceutical preparations that can be administered topically there come into consideration, especially, creams, ointments, pastes, foams, tinctures and solutions which contain from approximately 0.1 to approximately 10% of the active substance.

Creams are oil-in-water emulsions containing more than 50% of water. As oily bases there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Emulsifiers may be surface-active substances having predominantly hydrophilic properties, such as corresponding non-ionic emulsifiers, for example fatty acid esters of polyalcohols or ethylene oxide adducts thereof, such as polyglycerine fatty acid esters or polyoxyethylene sorbitan fatty acid esters (Tweens), and also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are normally used in the presence of fatty alcohols, for example cetyl alcohol or stearyl alcohol. Additives to the aqueous phase are, inter alia, agents that reduce the rate at which the creams dry out, for example polyalcohols, such as glycerine, sorbitol, propylene glycol and/or polyethylene glycols, and also preservatives, perfumes, etc.

Ointments are water-in-oil emulsions containing up to 70%, but preferably from about 20% to about 50%, of water or aqueous phases. The fatty phase may be especially hydrocarbons, for example, petroleum jelly, paraffin oil and/or hard paraffins which, in order to improve their water-binding ability, preferably contain suitable hydroxy compounds such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, moisture-retaining agents, such as polyalcohols, for example glycerine, propylene glycol, sorbitol and/or polyethylene glycol, and also preservatives, perfumes, etc.

Fatty ointments are water-free and contain as a base especially hydrocarbons, for example paraffin, petroleum jelly and/or liquid paraffins, and natural or partly synthetic fat, for example coconut fatty acid triglyceride, or preferably hardened oils, for example hydrogenated ground nut oil or castor oil, also fatty acid partial esters of glycerine, for example glycerine mono- and di-stearate, and also, for example, the fatty alcohols mentioned in connection with the ointments and which increase the water-absorbing capacity, and emulsifiers and/or additives.

Pastes are creams and ointments having secretion-absorbing powder constituents, such as metal oxides, for example titanium oxide or zinc oxide, and also talc and/or aluminium silicates, which have the function of binding moisture or secretions present.

Foams are administered, for example, from pressurised containers and are liquid oil-in-water emulsions in an aerosol form, the propellants used being halogenated hydrocarbons, such as chlorofluoro-lower alkanes, for example dichlorodifluoromethane and dichlorotetrafluoroethane. As the oily phase there are used, inter alia, hydrocarbons, for example paraffin oil, fatty alcohols, for example cetyl alcohol, fatty acid esters, for example isopropyl myristate, and/or other waxes. The emulsifiers used are, inter alia, mixtures of those having predominantly hydrophilic properties, such as polyoxyethylene sorbitan fatty acid esters (Tweens), and mixtures of those having predominantly lipophilic properties, such as sorbitan fatty acid esters (Spans). The customary additives, such as preservatives, etc., are also used.

Tinctures and solutions usually have an aqueous-ethanolic base to which are added, inter alia, polyalcohols, for example glycerine, glycols and/or polyethylene glycol, as moisture-retaining agents in order to reduce evaporation, fat-restoring substances, such as fatty acid esters with low polyethylene glycols, that is to say lipophilic substances soluble in the aqueous mixture, to replace the fatty substances withdrawn from the skin by the ethanol, and, if necessary, other adjuncts and additives.

The topically administrable pharmaceutical preparations are manufactured in a manner known per se, for example by dissolving or suspending the active substance in the base or, if necessary, in a part thereof. When the active substance is processed as a solution, it is as a rule dissolved in one of the two phases before emulsifying; when it is processed as a suspension, it is mixed with part of the base after emulsifying and then added to the rest of the formulation.

The following Examples illustrate the above-described invention, but are not intended to limit the scope thereof in any way. Temperatures are given in degrees Centigrade.

EXAMPLE 1

A mixture of 13.9 g of 1-phenyl-2-(3-pyridyl)-glyoxal, 9.5 g of α-formyl-α,α-dimethyl ethyl acetate (A. J. Meyers et al., J. Org. Chem. 38 (1) 41 (1973)), 35.6 g of ammonium acetate and 100 ml of glacial acetic acid is boiled under reflux for one hour and then poured, while stirring vigorously, into a mixture of 200 g of ice and 145 ml of concentrated aqueous ammonia solution. The crystal mass is extracted twice with 150 ml of ethyl acetate each time and the organic phase is washed neutral with water, dried with magnesium sulphate and evaporated to dryness under 11 torr at 40°. The residue is recrystallised from ether. 2-[4(5)-phenyl-5(4)-(3-pyridyl)-imidazol-2-yl]-2-methyl ethyl propionate is obtained in the form of white crystals having a melting point of 134° to 136°.

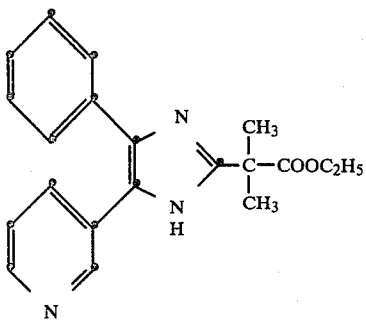

The following can be manufactured in an analogous manner:

2-[4(5)-phenyl-5(4)-(3-pyridyl)-imidazol-2-yl]-2-allyl ethyl acetate oil, starting from 1-phenyl-2-(3-pyridyl)-glyoxal and α-formyl-α-allyl ethyl acetate.

1-[4(5)-phenyl-5(4)-(3-pyridyl)-imidazol-2-yl]-1-ethoxycarbonylcyclopentane, melting point 115° to 117°, starting from 1-phenyl-2-(3-pyridyl)-glyoxal and 1-formyl-1-ethoxycarbonylcyclopentane.

2-[4(5)-(p-methoxyphenyl)-5(4)-(3-pyridyl)-imidazol-2-yl]-2-methyl ethyl propionate, melting point 126° to 128°, starting from 1-(p-methoxyphenyl)-2-(3-pyridyl)-glyoxal and α-formyl-α,α-dimethyl ethyl acetate.

EXAMPLE 2

0.5 g of palladium-carbon is added to a solution of 5 g of α-[4-phenyl-5-(3-pyridyl)-3-oxidoimidazol-2-yl]-2-methyl ethyl propionate in 50 ml of methylene chloride and then hydrogen is introduced while stirring. The reaction mixture is filtered and evaporated to dryness under 11 torr. The residue is extracted with ethyl acetate and washed with saturated sodium chloride solution. After drying over sodium sulphate and concentrating by evaporation under reduced pressure, the residue is crystallised from ether. 2-[4(5)-phenyl-5(4)-(3-pyridyl)-imidazol-2-yl]-2-methyl ethyl propionate having a melting point of 134° to 136° is obtained.

The starting material can be manufactured as follows:

A mixture of 6.0 g of α-hydroxyliminobenzyl-(3-pyridyl)-ketone, 6.5 g of 2-(2,2-dimethylethoxycarbonylmethyl)-4,4,6-trimethyl-2,3,5,6-tetrahydro-1,3-oxazine, 5.3 g of ammonium acetate and 26.5 ml of glacial acetic acid is boiled under reflux for 2 hours. It is then cooled and poured onto a mixture of 50 ml of concentrated aqueous ammonia and 100 g of ice. The suspension is filtered. The crystals are dissolved in 100 ml of ethyl acetate and the organic phase is extracted twice with 20 ml of water each time, dried over magnesium sulphate and concentrated to dryness under reduced pressure. The residue is crystallised from ethanol. The 2-[4-phenyl-5-(3-pyridyl)-3-oxidoimidazol-2-yl]-2-methyl ethyl propionate melts at 200° to 204°.

EXAMPLE 3

A mixture of 7.0 g of 1-phenyl-2-(1-oxido-3-pyridyl)-glyoxal, 4.5 g of α-formyl-α,α-dimethyl ethyl acetate, 17.8 g of ammonium acetate and 50 ml of glacial acetic acid is boilded for one hour under reflux and then poured, while stirring, into a mixture of 100 g of ice and 70 ml of concentrated aqueous ammonia solution. The oil which separates out is extracted twice with 70 ml of ethyl acetate each time and the organic phase is washed neutral with water, dried over magnesium sulphate and evaporated to dryness under 11 torr at 40°. The residue is recrystallised from methanol/water. The 2-[4(5)-phenyl-5(4)-(1-oxido-3-pyridyl)-imidazol-2-yl]-2-methyl ethyl propionate (in the formm of a monohydrate) melts at 82° to 85°.

EXAMPLE 4

A mixture of 38.9 g of 1-phenyl-2-(3-pyridyl)-glyoxal, 44.6 g of 2-(2,2-dimethylethoxycarbonylmethyl)-4,4,6-trimethyl-2,3,5,6-tetrahydro-1,3-oxazine, 99.1 g of ammonium acetate and 275 ml of glacial acetic acid is heated under reflux for 3 hours while introducing nitrogen, and is cooled and poured, while stirring, into a mixture of 900 g of ice and 550 ml of concentrated aqueous ammonia solution. The suspension is extracted twice with 700 ml of ethyl acetate each time and the organic phase is washed with 500 ml of water, dried over magnesium sulphate and evaporated to dryness at 40° under reduced pressure. The residue is crystallised from ether. The 2-[4(5)-phenyl-5(4)-(3-pyridyl)-imidazol-2-yl]-2-methyl ethyl propionate melts at 134° to 136°.

The following can be manufactured in an analogous manner:

2-[4(5)-phenyl-5(4)-(3-pyridyl)-imidazol-2-yl]-ethyl propionate hemihydrate, oil, starting from 1-phenyl-2-(3-pyridyl)-glyoxal and 2-(2-methylethoxycarbonylmethyl)-4,4,6-trimethyl-2,3,5,6-tetrahydro-1,3-oxazine.

2-[4(5)-phenyl-5(4)-(3-pyridyl)-imidazol-2-yl]-ethyl acetate, yellow oil, starting from 1-phenyl-2-(3-pyridyl)-glyoxal and 2-(ethoxycarbonylmethyl)-4,4,6-trimethyl-2,3,5,6-tetrahydro-1,3-oxazine.

2-[4(5)-phenyl-5(4)-(3-pyridyl)-imidazol-2-yl]-2-allyl ethyl acetate, melting point 106° to 108° (from ethyl acetate/ether), starting from 1-phenyl-2-(3-pyridyl)-glyoxal and 2-(2-allylethoxycarbonylmethyl)-4,4,6-trimethyl-2,3,5,6-tetrahydro-1,3-oxazine.

1-[4(5)-phenyl-5(4)-(3-pyridyl)-imidazol-2-yl]-1-ethoxycarbonylcyclopentane, melting point 115° to 117°, starting from 1-phenyl-2-(3-pyridyl)-glyoxal and 1-ethoxycarbonyl-1-(4,4,6-trimethyl-2,3,5,6-tetrahydro-1,3-oxazin-2-yl)-cyclopentane.

2-[4(5)-(p-methoxyphenyl)-5(4)-(3-pyridyl)-imidazol-2-yl]-2-methyl ethyl propionate, melting point 125° to 128° (from ether), starting from 1-(p-methoxyphenyl)-2-(3-pyridyl)-glyoxal and 2-(2,2-dimethylethoxycarbonylmethyl)-4,4,6-trimethyl-2,3,5,6-tetrahydro-1,3-oxazine.

2-[4(5)-(m-methoxyphenyl)-5(4)-(3-pyridyl)-imidazol-2-yl]-2-methyl ethyl propionate, melting point 135° to 137° (from ethyl acetate/ether), starting from 1-(m-methoxyphenyl)-2-(3-pyridyl)-glyoxal and 2-(2,2-dimethylethoxycarbonylmethyl)-4,4,6-trimethyl-2,3,5,6-tetrahydro-1,3-oxazine.

2-[4(5)-(3,4-dimethoxyphenyl)-5(4)-(3-pyridyl)-imidazol-2-yl]-2-methyl ethyl propionate, melting point 144° to 146° (from ethyl acetate/ether) starting from 1-(3,4-dimethoxyphenyl)-2-(3-pyridyl)-glyoxal and 2-(2,2-dimethylethoxycarbonylmethyl)-4,4,6-trimethyl-2,3,5,6-tetrahydro-1,3-oxazine.

2-[4-(5)-(p-chlorophenyl)-4(4)-(3-pyridyl)-imidazol-2-yl]-2-methyl ethyl propionate, melting point 161° to 163° (from methylene chloride/n-hexane), starting from 1-(p-chlorophenyl)-2-(3-pyridyl)-glyoxal and 2-(2,2-dimethylethoxycarbonylmethyl)-4,4,6-trimethyl-2,3,5,6-tetrahydro-1,3-oxazine.

2-[4(5)-phenyl-5(4)-(4-pyridyl)-imidazol-2-yl]-2-methyl ethyl propionate, melting point 210° to 212° (from ethyl acetate/ether), starting from 1-phenyl-2-(4-pyridyl)-glyoxal and 2-(2,2-dimethylethoxycarbonyl-methyl)-4,4,6-trimethyl-2,3,5,6-tetrahydro-1,3-oxazine.

EXAMPLE 5

A mixture of 7.14 g of α-bromo-(3-pyridyl)-benzyl ketone hydrobromide and 19.56 g of methyl monoethyl malonate ammonium salt in 30 ml of anhydrous dimethylformamide is heated for 5 hours at 100° while stirring and introducing nitrogen. The mixture is then cooled and concentrated to dryness under 11 torr at a bath temperature of 70°. 300 ml of ethyl acetate and 200 ml of water are added to the residue. The mixture is adjusted to pH 8 to 9 with concentrated aqueous ammonia solution. The organic phase is separated off, washed twice with 50 ml of water each time, dried over magnesium sulphate and evaporated to dryness under 11 torr. The residue is chromatographed over 100 g of silica gel. Fractions 1 to 8, each eluted with 600 ml of chloroform, are discarded. Fractions 9 to 16, each eluted with 600 ml of chloroform/methanol (99:2), are combined and evaporated to dryness under 11 torr. The residue, 2-[4(5)-phenyl-5(4)-(3-pyridyl)-imidazol-2-yl]-ethyl propionate, is in the form of a yellow oil.

The following can be manufactured in an analogous manner:

2-[4(5)-phenyl-5(4)-(1-oxido-3-pyridyl)-imidazol-2-yl]-2-methyl ethyl butyrate, starting from α-bromo-(1-oxido-3-pyridyl)-benzyl ketone and 2-ethyl-2-methyl-monoethyl malonate ammonium salt.

2-[4(5)-phenyl-5(4)-(3-pyridyl)-imidazol-2-yl]-2-methyl ethyl propionate, melting point 134° to 136° (from ether), starting from α-bromo-(3-pyridyl)-benzyl ketone and dimethyl monoethyl malonate ammonium salt.

The starting material is manufactured as follows:

A solution of 42.5 g of benzyl-(3-pyridyl)-ketone in 400 ml of ethylene chloride is heated to 50°. At this temperature a solution of 36.2 g of bromine in 30 ml of ethylene chloride is added dropwise. The suspension is stirred for 15 hours at 50° and then cooled and filtered. The crystals which have been filtered off are washed three times with 30 ml of ethylene chloride each time and dried at 50° under 0.1 torr. The α-bromobenzyl-(3-pyridyl)-ketone hydrobromide melts at 218° to 219.5°.

EXAMPLE 6

46.0 g of N-[4-methoxy-α-(p-methoxyphenyl)-phenacyl]-monoethyl malonate amide are boiled under reflux for two hours with 70.1 g of ammonium acetate in 400 ml of glacial acetic acid. The solution is then poured onto 800 ml of concentrated ammonia and 900 g of ice and extracted with ethyl acetate. The organic phase is separated off, washed neutral with saturated sodium chloride solution, dried over magnesium sulphate and concentrated by evaporation under reduced pressure at 40°. The residue is dissolved in 500 ml of an ether/ethyl acetate mixture (9:1). The solution is filtered through a layer of silica gel. The filtrate is concentrated under reduced pressure at 40°. The residue is crystallised from ethyl acetate/ether. The 2-[4,5-bis-(p-methoxyphenyl)-imidazol-2-yl]-ethyl acetate melts at 131° to 132°.

The following can be manufactured in an analogous manner:

2-[4,5-bis-(p-methoxyphenyl)-imidazol-2-yl]-2-methyl ethyl propionate, oil, starting from N-[4-methoxy-60-(p-methoxyphenyl)-phenacyl]-dimethyl monoethyl malonate amide.

2-[4(5)-phenyl-5(4)-(3-pyridyl)-immidazol-2-yl]-2-methyl ethyl propionate, melting point 134° to 136° (from ether), starting from N-[α-(3-pyridylcarbonyl)-benzyl]-dimethyl monoethyl malonate amide.

The starting material can be manufactured as follows:

18 ml of triethylamine are added while stirring to a suspension of 17.8 g of 2-amino-4'-methoxy-2-(p-methoxyphenyl)-acetophenone hydrochloride in 150 ml of anhydrous benzene. 9.6 g of monoethyl malonate chloride are then added dropwise in the course of 15 minutes, while cooling with ice, is such a manner that the internal temperature does not exceed 20°. After a further 10 minutes, 9 ml of triethylamine are added. The suspension is stirred for 16 hours at 20° to 25°, then water is added and the mixture is diluted with ethyl acetate. The organic phase is separated off, washed with 2N sodium carbonate solution, saturated sodium chloride solution and with water, dried over magnesium sulphate and evaporated to dryness under reduced pressure at 40°. The residue is crystallised from ethyl acetate/ether. The N-[4-methoxy-60-(p-methoxyphenyl)-phenacyl]-monoethyl malonate amide melts at 96° to 97°.

The following can be manufactured in an analogous manner:

N-[4-methoxy-60-(p-methoxyphenyl)-phenacyl]-dimethyl monoethyl malonate amide, starting from 2-amino-4'-methoxy-2-(p-methoxyphenyl)-acetophenone hydrochloride and dimethyl monoethyl malonate chloride.

N-[α-(3-pyridylcarbonyl)-benzyl]-dimethyl monoethyl malonate amide, oil, starting from α-aminobenzyl-(3-pyridyl)-ketone and dimethyl monoethyl malonate chloride.

α-aminobenzyl-(3-pyridyl)-ketone can be manufactured in the following manner:

10.8 g of benzyl-(3-pyridyl)-ketone are stirred for 6 hours at 100° together with 40 ml of pyridine and a solution of 8 g of hydroxylamine hydrochloride in 15 ml of pyridine. The reaction mixture is poured onto ice-water and then stirred for 15 minutes. The precipitated crystals are filtered off with suction, washed with water and dried under a high vacuum. Benzyl-(3-pyridyl)-ketone oxime having a melting point of 122° to 126°.

A solution of 7.7 g of p-toluene sulphochloride in 15 ml of pyridine is added dropwise in the course of 5 minutes to a solution, stirred at −10°, of 8.5 g of benzyl-(3-pyridyl)-ketone oxime in 20 ml of pyridine. The reaction mixture is stored for 24 hours in an ice box and then poured onto ice-water. After stirring and triturating for a short period, the oil that separates out solidifies to form crystals. These are filtered off with suction, washed with water and dried under a high vacuum. Benzyl-(3-pyridyl)-ketone oxime p-toluene sulphonate is obtained and is used without further purification in the next stage.

11.6 g of crude benzyl-(3-pyridyl)-ketone oxime p-toluene sulpho-ester are suspended in 90 ml of absolute ethanol. A solution of 3.7 g of potassium tert.-butoxide in 30 ml of absolute ethanol is then added dropwise at 0° while stirring. The reaction mixture is stirred for 2 hours at 0°. The suspension is filtered off with suction and the filrate, which contains the desired α-aminobenzyl-(3-pyridyl)-ketone, is immediately subjected to further reaction in the next stage.

EXAMPLE 7

1.7 g of 2-[1-benzyl-4(5)-phenyl-5(4)-(3-pyridyl)-imidazol-2-yl]-2-methyl ethyl propionate are dissolved in 40 ml of methylene chloride and, after the addition of 0.6 g of palladium-carbon, the solution is hydrogenated at room temperature. When the absorption of hydrogen is complete, the catalyst is filtered off and the filtrate is concentrated to dryness under 11 torr at 40°.

The residue is crystallised from ether. 2-[4(5)-phenyl-5(4)-(3-pyridyl)-imidazol-2-yl]-2-methyl ethyl propionate melts at 134° to 136°.

The following can be manufactured in an analogous manner:

The sodium salt of 2-[4(5)-phenyl-5(4)-(3-pyridyl)-imidazol-2-yl]-2-methylpropionic acid, in the form of a hydrate, melting point 273° to 276°, starting from 2-[1-benzyl-4(5)-phenyl-5(4)-(3-pyridyl)-imidazol-2-yl]-2-methylpropionic acid.

The starting materials can be manufactured as follows:

A mixture of 3.5 g of α-bromo-(3-pyridyl)-benzyl ketone hydrobromide and 9.68 g of 3-ethoxypivalic acid ammonium salt in 25 ml of anhydrous dimethylformamide is heated for 6 hours at 100° while stirring and introducing nitrogen. The mixture is cooled and evaporated to dryness under 11 torr at a bath temperature of 60°. 140 ml of ethyl acetate and 100 ml of water are added to the residue. The pH of the mixture is adjusted to from 8 to 9 with concentrated aqueous ammonia solution. The ethyl acetate solution is separated off, washed twice with 30 ml of water each time, dried over magnesium sulphate and evaporated to dryness under 11 torr. The residue is chromatographed over 60 g of silica gel. Fractions 1 to 4, each eluted with 250 ml of chloroform, are discarded. Fractions 5 to 12, each eluted with 250 ml of chloroform/methanol (99:2), are combined and evaporated to dryness under 11 torr. The residue, 2-[4(5)-phenyl-5(4)-(3-pyridyl)-imidazol-2-yl]-2-methyl-1-ethoxypropane, is in the form of an oil.

0.25 of sodium hydride mineral oil dispersion is added at 0° to a solution of 1.5 g of 2-[4(5)-phenyl-5(4)-(3-pyridyl)-imidazol-2-yl]-2-methyl-1-ethoxypropane in 15 ml of anhydrous dimethylformamide. The mixture is stirred for 1 hour at room temperature while introducing nitrogen and then a solution of 0.65 ml of benzyl bromide in 7.0 g of anhydrous dimethylformamide is added dropwise. The mixture is stirred for 30 minutes at room temperature and then poured onto 100 ml of ice-water. The oil which separates out is extracted three times with 80 ml of ethyl acetate each time. The combined organic phases are washed with water, dried over magnesium sulphate and evaporated to dryness under 11 torr at room temperature. The residue is chromatographed over 40 g of silica gel. Fractions 1 to 5, each eluted with 100 ml of chloroform, are discarded. Fractions 6 to 10, each eluted with 100 ml of chloroform/methanol (99.1), contain 2-[1-benzyl-4(5)-phenyl-5(4)-(3-pyridyl)-imidazol-2-yl]-2-methyl-1-ethoxypropane. They are combined and evaporated to dryness under 11 torr at room temperature. The residue is in the form of an oil.

Potassium permanganate is added in portions at room temperature and while stirring rapidly to a solution of 1.3 g of 2-[1-benzyl-4(5)-phenyl-5(4)-(3-pyridyl)-imidazol-2-yl]-2-methyl-1-ethoxypropane in 30 ml of acetone and 10 ml of water under decoloration ceases. The mixture is stirred for 10 hours at room temperature and filtered. The filtrate is concentrated to dryness under 11 torr at 50°. 10 ml of ice-water are added to the residue and the oil which separates out is extracted with ethyl acetate. The organic phase is washed with saturated sodium chloride solution. After drying over sodium sulphate and filtering through a layer of silica gel, the filtrate is concentrated to dryness under 11 torr at room temperature. The residue is triturated with ether. After drying under 0.1 torr at room temperature, the 2-[1-benzyl-4(5)-phenyl-5(4)-(3-pyridyl)-imidazol-2-yl]-2-methyl ethyl propionate is in the form of a solid foam.

EXAMPLE 8

40 ml of 0.5N sodium hydroxide solution are added to a solution of 3.32 g of 2-[4(5)-phenyl-5(4)-(3-pyridyl)-imidazol-2-yl]-2-methyl ethyl propionate in 20 ml of methanol. The solution is stirred for 4 hours at room temperature and concentrated by evaporation under reduced pressure at 40°. 50 ml of methylene chloride are added to the residue and the yellowish crystals are filtered off. The sodium salt of 2-[4(5)-phenyl-5(4)-(3-pyridyl)-imidazol-2-yl]-2-methyl propionic acid (in the form of a hydrate) melts at 273° to 276°.

The following can be manufactured in an analogous manner:

2-[4,5-bis-(-p-methoxyphenyl)-imidazol-2-yl]-acetic acid sodium salt monohydrate, melting point 187° to 190°, starting from 2-[4,5-bis-(p-methoxyphenyl)-imidazol-2-yl]-ethyl acetate.

EXAMPLE 9

3.0 ml of 1N sodium hydroxide solution are added while stirring to a solution of 0.9 g of 2-[4(5)-phenyl-5(4)-(1-oxido-3-pyridyl)-2-yl]-2-methyl ethyl propionate in 10 ml of methanol. The solution is stirred for 15 hours at room temperature and freed of methanol under 11 torr at 40°. 20 ml of water are added to the residue and the yellow solution is extracted with 20 ml of chloroform. The aqueous phase is then separated off and acidified at 0° with 2N hydrochloric acid. The clear solution is extracted with 10 ml of chloroform. The aqueous phase is then evaporated to dryness under 11 torr at 40°. The white crystalline residue is dried under 0.1 torr at room temperature for 20 hours. The 2-[4(5)-phenyl-5(4)-(1-oxido-3-pyridyl)-imidazol-2-yl]-2-methylpropionic acid melts at 178° to 180°.

EXAMPLE 10

A solution of 5.9 g of 2-[4(5)-phenyl-5(4)-(3-pyridyl)-imidazol-2-yl]-2-methyl ethyl propionate in 120 ml of methylene chloride is cooled to from 0° to 5° and 3.5 g of m-chlorobenzoic acid are added. The mixture is stirred for 24 hours at room temperature. The yellow solution is then washed twice with 20 ml of 2N potassium bicarbonate solution each time and once with 30 ml of water, dried over magnesium sulphate and concentrated at 40° under reduced pressure. The residue is dissolved in a little methanol. After the addition of water, the 2-[4(5)-phenyl-5(4)-(1-oxido-3-pyridyl)-imidazol-2-yl]-2-methyl ethyl propionate crystallises in the form of a monohydrate. Melting point 82° to 85°.

The following can be manufactured in an analogous manner:

2-[4(5)-phenyl-5(4)-(1-oxido-3-pyridyl)-imidazol-2-yl]-2-methyl methyl propionate monohydrate, melting point 96° to 98° (from methanol/water).

2-[4(5)-phenyl-5(4)-(1-oxido-4-pyridyl)-imidazol-2-yl]-2-methyl ethyl propionate, melting point 164° to 166°

(from ethyl acetate), starting from 2-[4(5)-phenyl-5(4)-(4-pyridyl)-imidazol-2-yl]-2-methyl ethyl propionate.

2-[4(5)-phenyl-5(4)-(1-oxido-3-pyridyl)-imidazol-2-yl]-ethyl propionate hemihydrate, oil, starting from 2-[4(5)-phenyl-5(4)-(3-pyridyl)-imidazol-2-yl]-ethyl propionate.

1-4(5)-phenyl-5(4)-(1-oxido-3-pyridyl)-imidazol-2-yl]-1-ethoxycarbonylcyclopentane, oil, starting from 1-[4(5)-phenyl-5(4)-(3-pyridyl)-imidazol-2-yl]-1-ethoxycarbonylcyclopentane.

2-[4(5)-(p-chlorophenyl)-5(4)-(1-oxido-3-pyridyl)-imidazol-2-yl]-2-methyl ethyl propionate, melting point 137° to 140° (from methylene chloride/petroleum ether), starting from 2-[4(5)-(p-chlorophenyl)-5(4)-(3-pyridyl)-imidazol-2-yl]-2-methyl ethyl propionate.

EXAMPLE 11

Under a nitrogen atmosphere, a solution of 4.7 g of boron tribromide in 20 ml of methylene chloride is added dropwise in the course of 3 minutes while stirring at −70° to a solution of 1.3 g of 2-[4(5)-(p-methoxyphenyl)-5(4)-(3-pyridyl)-imidazol-2-yl]-2-methyl ethyl propionate in 50 ml of methylene chloride. The mixture is stirred for 30 minutes at −70°. The cooling bath is then removed and stirring is continued until the internal temperature has reached 25°. The white suspension is then poured onto 50 ml of a mixture of ice and water and stirred. The aqueous phase is separated off, extracted twice with 20 ml of methylene chloride each time and adjusted to pH 8 with 2N sodium carbonate solution. The precipitated crystals are extracted twice with 30 ml of ethyl acetate each time. The combined ethyl acetate phases are dried over magnesium sulphate and evaporated to dryness under reduced pressure. The residue is crystallised from ethyl acetate/ether. The 2-[4(5)-(p-hydroxyphenyl)-5(4)-(3-pyridyl)-imidazol-2-yl]-2-methyl ethyl propionate melts at 186° to 187°.

EXAMPLE 12

5.0 g of 2-[4,5-bis-(p-methoxyphenyl)-imidazol-2-yl]-propionic acid are added to 100 ml of anhydrous methanol saturated with hydrochloric acid gas. The mixture is heated under reflux for 15 hours, cooled and evaporated to dryness under reduced pressure. 10 ml of water are added to the residue and the mixture is rendered alkaline with aqueous concentrated ammonia solution. Extraction is effected twice with 40 ml of ethyl acetate each time and the organic phase is washed at 5° with 20 ml of 2N potassium bicarbonate solution and 20 ml of water, dried over magnesium sulphate and concentrated to dryness under reduced pressure. The 2-[4,5-bis-(p-methoxyphenyl)-imidazol-2-yl]-methyl propionate crystallises from ether/petroleum ether.

EXAMPLE 13

3.0 g of diethyl sulphate are added at 80° while stirring to a solution of 3.52 g of the potassium salt of 2-[4,5-bis(p-methoxyphenyl)-imidazol-2-yl]-propionic acid in 30 ml of anhydrous dimethylformamide. The mixture is stirred for 15 minutes at 80°, cooled and poured onto ice-water. The oil which separates out is dissolved in ethy acetate and the organic phase is extracted twice with 2N potassium bicarbonate solution, dried over magnesium sulphate and evaporated to dryness under reduced pressure. The 2-[4,5-bis-(p-methoxyphenyl)-imidazol-2-yl]-ethyl propionate is crystallised from ether/petroleum ether.

The following can be manufactured in an analogous manner:

2-[4(5)-phenyl-5(4)-(3-pyridyl)-imidazol-2-yl]-2-methyl methyl propionate, melting point 158° to 162° (from ether).

EXAMPLE 14

2.5 g of pivaloyloxymethyl iodide are added dropwise at room temperature, while introducing nitrogen and stirring, to a suspension of 3.5 g of 2-[4(5)-phenyl-5(4)-(3-pyridyl)-imidazol-2-yl]-2-methylpropionic acid sodium salt monohydrate in 50 ml of anhydrous dimethylformamide. The mixture is stirred for 15 hours at room temperature and then evaporated to dryness under 11 torr. The residue is partitioned between 20 ml of water and 50 ml of ethyl acetate. The organic phase is separated off, dried over magnesium sulphate and concentrated to dryness under 11 torr. The residue is chromatographed over 300 g of silica gel. Fractions 1 to 15, each eluted with 300 ml of chloroform/ethyl acetate (95:5), are discarded. Fractions 16 to 26, each eluted with 300 ml of chloroform/ethyl acetate (80:20), are combined and evaporated to dryness under 11 torr. The residue is crystallised from ether/petroleum ether. The 2-[4(5)-phenyl-5(4)-(3-pyridyl)-imidazol-2-yl]-2-methyl pivaloyloxymethyl propionate melts at 143° to 145°.

EXAMPLE 15

A solution of 5.0 g of 2-[4,5-bis-(p-methoxyphenyl)-imidazol-2-yl]-propionic acid amide and 5.0 g of potassium hydroxide in 100 ml of n-butanol is heated under reflux for 8 hours. It is then cooled and evaporated to dryness under 0.1 torr at 50°. The residue is dissolved in 200 ml of water. The solution is filtered and the filtrate is acidified with concentrated hydrochloric acid. The precipitated crystals, 2-[4,5-bis-(p-methoxyphenyl)-imidazol-2-yl]-propionic acid, are filtered off.

The following can be manufactured in an analogous manner:

2-[4,5-bis-(p-methoxyphenyl)-imidazol-2-yl]-acetic acid, starting from 2-[4,5-bis-(p-methoxyphenyl)-imidazol-2-yl]-acetic acid amide.

The starting material can be manufactured as follows:

Sodium is added in portions to a solution of 10 g of 2-[1-benzyl-4,5-bis-(p-methoxyphenyl)-imidazol-2-yl]-ethyl propionate in 150 ml of liquid ammonia until the colour of the solution remains blue. The solution is stirred for a further 45 minutes and the sodium amide excess is decomposed by the addition of ammonium chloride. The cooling bath is removed and the ammonia is allowed to evaporate off. 100 ml of ice-water are added to the solid residue and the crystalline 2-[4,5-bis-(p-methoxyphenyl)-imidazol-2-yl]-propionic acid amide is filtered off.

11.1 g of 2-[4,5-bis-(p-methoxyphenyl)-oxazol-2-yl]-ethyl acetate are heated with 97.0 g of liquid ammonia and 64 g of formamide for 5 hours at 200° in an autoclave. (The pressure is 185 atmospheres gauge). The reaction mixture is cooled and poured onto 300 ml of water. The oil which separates out is extracted with 150 ml of ethyl acetate. The organic phase is separated off, washed with 30 ml of saturated sodium chloride solution and water, dried over magnesium sulphate and evaporated to dryness under reduced pressure. 2-(4,5-bis-(p-methoxyphenyl)-imidazol-2-yl]-acetic acid amide is crystallised from methanol.

EXAMPLE 16

Hydrochloric acid gas is introduced at 0° into a solution of 1.0 g of 2-(4(5)-phenyl-5(4)-(3-pyridyl)-imidazol-2-yl]-2-methylpropionitrile in 15 ml of anhydrous ether and 20 ml of anhydrous ethanol. After 3 hours the temperature is increased to 20° and hydrochloric acid gas is introduced for a further hour. The mixture is left to stand for 15 hours and is then concentrated to dryness under reduced pressure. 10 ml of water and 20 ml of ether are added to the residue and the mixture is heated for 2½ hours at 40°. It is then cooled and 2 N sodium hydroxide solution is added until the pH is 7.5. The organic phase is separated off, washed with water, dried over magnesium sulphate and concentrated to dryness under 11 torr at 40°. The residue is crystallised from ether. The 2-[4(5)-phenyl-5(4)-(3-pyridyl)-imidazol-2-yl]-2-methyl ethyl propionate melts at 134° to 136°.

The starting material can be manufactured as follows:

A mixture of 3.3 g of α-bromo-(3-pyridyl)-benzyl ketone hydrobromide and 10 g of 2-cyano-2-methylpropionic acid ammonium salt in 20 ml of anhydrous dimethylformamide is heated for 6 hours at 100° while stirring and introducing nitrogen. After cooling, the mixture is concentrated to dryness under 11 torr at a temperature of 70°. 200 ml of ethyl acetate and 150 ml of water are added to the residue. The reaction mixture is then adjusted to pH 8 to 9 with concentrated aqueous ammonia solution. The organic phase is separated off, washed twice with 40 ml of water each time, dried over magnesium sulphate and evaporated to dryness under 11 torr at room temperature. The residue is chromatographed over 100 g of silica gel. The first 8 fractions, each eluted with 600 ml of chloroform, are discarded and fractions 9 to 18, eluted with chloroform/methanol (99:1), are combined and evaporated to dryness under 11 torr. 2-[4(5)-phenyl-5(4)-(3-pyridyl)-imidazol-2-yl]-2-methylpropionitrile is obtained and further reacted without further purification.

EXAMPLE 17

A solution of 2.0 g of 2-[4(5)-phenyl-5(4)-(3-pyridyl)-imidazol-2-yl]-acetaldehyde dimethyl acetal in 25 ml of dioxan and 10 ml of water is heated to 60° and 0.2 ml of methanesulphonic acid is added. The solution is heated for one hour at 80°, cooled and poured onto ice-water. The pH is adjusted to 8.0 with concentrated aqueous ammonia solution and the oil which separates out is extracted with 50 ml of ethyl acetate. The organic phase is separated off, washed twice with 10 ml of water each time, dried over magnesium sulphate and evaporated to dryness under reduced pressure. The residue, 2-[4(5)-phenyl-5(4)-(3-pyridyl)-imidazol-2-yl]-acetaldehyde, is in the form of a yellow oil.

The starting material can be manufactured as follows:

A mixture of 30.0 g of α-bromobenzyl-(3-pyridyl)-ketone hydrobromide and 50.0 g of the ammonium salt of malonic aldehyde acid dimethyl acetal in 180 ml of anhydrous dimethylformamide is heated at 100° for 4 hours while stirring and introducing nitrogen gas. The mixture is then cooled and evaporated to dryness under 11 torr at 70°. 100 ml of water and 400 ml of ethyl acetate are added to the residue. The pH is adjusted to 8.0 by adding concentrated aqueous ammonia solution. The organic phase is separated off, washed with 50 ml of water, dried over magnesium sulphate and evaporated to dryness under 11 torr. The residue is chromatographed over 500 g of silica gel. Fractions 1 to 4, each eluted with 600 ml of chloroform, are discarded. Fractions 5 to 16, each eluted with 600 ml of chloroform/methanol (98:2), are combined and evaporated to dryness under reduced pressure. The residue, N-[α-(3-pyridyl)-phenacyl)-malonic aldehyde acid dimethyl acetal amide, is in the form of a yellow oil.

Fractions 19 to 24, each eluted with 600 ml of chloroform/methanol (97:3) are combined and evaporated to dryness under reduced pressure. The residue is crystallised from ether/petroleum ether. The 2-[4(5)-phenyl-5(4)-(3-pyridyl)-imidazol-2-yl]-acetaldehyde dimethyl acetal melts at 142° to 145°.

A mixture of 10.0 g of N-[α-(3-pyridyl)-phenacyl]-malonic aldehyde acid dimethyl acetal amide, 30.0 g of ammonium acetate and 100 ml of glacial acetic acid is boiled under reflux for 2 hours and then poured while stirring vigorously into a mixture of 200 g of ice and 150 ml of concentrated aqueous ammonia solution. The crystal mass is extracted twice with 150 ml of ethyl acetate each time and the organic phase is washed neutral with water, dried with magnesium sulphate and evaporated to dryness under 11 torr at 40°. The residue is chromatographed over 500 g of silica gel. Fractions 1 to 4, each eluted with 500 ml of chloroform/methanol (99:1), are discarded. Fractions 5 to 15, each eluted with 500 ml of chloroform/methanol (99:2), are combined and evaporated to dryness under reduced pressure. The residue is crystallised from ether/petroleum ether. The 2-[4(5)-phenyl-5(4)-(3-pyridyl)-imidazol-2-yl]-acetaldehyde dimethyl acetal melts at 142° to 145°.

The starting material is manufactured as follows:

19.7 g of malonic aldehyde acid dimethyl acetal (V. V. Shikina et al. J. Gen. Chem. U.S.S.R. 25, 723–725 (1955)) are dissolved in 300 ml of anhydrous ether. Ammonia gas is introduced into the solution at 0° for one hour. The mixture is then evaporated to dryness under reduced pressure. The ammonium salt of the malonic aldehyde acid dimethyl acetal is in the form of an oil.

EXAMPLE 18

5.5 g of iodine are added while stirring to a solution of 5.0 g of Z-[4(5)-(3-pyridyl)-imidazol-2-yl]-acetaldehyde in 50 ml of methanol. A 4% methanolic potassium hydroxide solution is added dropwise to the mixture at 50° until decoloration occurs. 10 ml of 2 N potassium hydroxide solution are added to saponify the ester formed. The solution is heated for 10 minutes at 50° and evaporated to dryness under reduced pressure.

EXAMPLE 19

2.2 g of 2,3-bis-(p-methoxyphenyl)-2H-azirine, dissolved in 15 ml or ethyl cyanoacetate, are added dropwise at 0°, while stirring and while introducing nitrogen, to a solution of 2 mmol of boron trifluoride diethyl etherate in 10 ml of ethyl cyanoacetate. The mixture is stirred for approximately 5 hours at this temperature and then poured into a 5% aqueous sodium bicarbonate solution. The reaction mixture is extracted 3 times with 70 ml or methylene chloride each time. The methylene chloride phase is dried over anhydrous magnesium sulphate, filtered and concentrated by evaporation in vacuo. The nitrile excess is then removed by distillation under a high vacuum. After recrystallisation from ethyl acetate/ether, 2-[4,5-bis-(p-methoxyphenyl)-imidazol-2-yl]-ethyl acetate is obtained and has a melting point of 131 to 132°.

The starting material can be manufactured analogously to the procedure described in J. Amer. Chem. Soc., 89, 2077f (1967). For example, 1-azido-1-iodo-1,2-bis-(p-methoxyphenyl)-ethane is used as the starting material for the manufacture of 2,3-bis-(p-methoxyphenyl)-2-H-azine (via 1-azido-1,2-bis-(p-methoxyphenyl)-ethene).

Example 20

A mixture of 1.8 g of 2-(trans-4,5-(p-methoxyphenyl)-4,5-dihydroimidazolin-2-yl)-2-methylpropionic acid amide and 2.0 g of 2,3-dichloro-5,6-dicyano-1,4-benzoquinone in 60 ml of anhydrous dioxan is heated under reflux for 5 hours. The mixture is cooled, filtered and the filtrate is concentrated to dryness under reduced pressure at 40°. The residue is dissolved in 50 ml of ethyl acetate. The ethyl acetate solution is washed with 20 ml of water, twice with 20 ml of 2N sodium carbonate solution each time and again with 20 ml of water, dried over magnesium sulphate, filtered through a layer of silica gel and evaporated to dryness under reduced pressure at 40°. The 2-(4,5-bis-(p-methoxyphenyl)-imidazol-2-yl]-2-methylpropionic acid amide crystallises from ethanol/water.

The starting material can be manufactured as follows:

A solution of 2.7 g of dl-1,2-bis-(4-methoxyphenyl)-ethylenediamine and 1.6 g of dimethyl monoethyl malonate monoamide in 40 ml of diphenyl ether is heated for 3 hours at 150°. The ethyl alcohol formed is distilled off. The solution is then cooled, poured onto 100 ml of water and the oil which separates out is extracted twice with 100 ml of ether each time. The combined organic phases are washed with 50 ml of water, dried over magnesium sulphate and freed of ether under 11 torr at 30° and then of the remaining diphenyl ether under 0.1 torr at 60°. The 2-[trans-9,5-(p-methoxyphenyl)-4,5-dihydroimidazol-2yl]-2-methylpropionic acid amide is in the form of an oil and, moreover, is further reacted.

EXAMPLE 21

A mixture of 2.7 g of 4,4'-dimethoxystilbenediamine and 1.2 g of dimethylmalonic acid aldehyde monoamide in 50 ml of nitrobenzene is heated under reflux for 40 minutes. The solution is cooled and evaporated to dryness under 0.1 torr at 60°. The residue, 2-[4,5-bis-(p-methoxyphenyl)imidazol-2-yl]-2-methylpropionic acid amide crystallises from ethanol/water.

EXAMPLE 22

Potassium permanganate is added in portions at room temperature while stirring vigorously to a solution of 3.8 g of 2-[4(5)-phenyl-5(4)-(3-pyridyl)-imidazol-2-yl]-2-methyl-1-ethoxypropane in 80 ml of acetone and 25 ml of water until no further decoloration is observed. The mixture is then stirred for 10 hours at room temperature and afterwards filtered. The filtrate is concentrated to dryness under 11 torr at 50°. 20 ml of ice-water are added to the residue and extraction is effected with ethyl acetate. The organic phase is washed with saturated sodium chloride solution, dried over sodium sulphate and filtered through a layer of silica gel. The filtrate is then concentrated under 11 torr at room temperature. The residue is recrystallised from ether. 2-[4(5)-phenyl-5(4)-(3-pyridyl)-imidazol-2-yl]-2-methyl ethyl propionate is obtained, melting point 134 to 136°.

EXAMPLE 23:

An ointment containing 5% 2-[4(5)-phenyl-5(4)-(1-oxido-3-pyridyl)-imidazol-2-methyl ethyl propionate can be manufactured as follows:

| Composition | |
|---|---|
| active substance | 5.0% |
| petroleum jelly | 45.0% |
| paraffin oil | 19.6% |
| cetyl alcohol | 5.0% |
| beeswax | 5.0% |
| sorbitan sesquioleate | 5.0% |
| p-hydroxybenzoic acid ester | 0.2% |
| water | 20.0% |

The fats and emulsifiers are melted together. The preservative is dissolved in water and the solution is incorporated into the fatty melt by emulsification at elevated temperature. After cooling, a suspension of the active substance in part of the fatty melt is incorporated into the emulsion.

EXAMPLE 24

A cream containing 10% (2-[4(5)-phenyl-5(4)-(3-pyridyl)-imidazol-2-yl]-2-methyl ethyl propionate can be manufactured as follows:

| Composition | |
|---|---|
| active substance | 10.0% |
| isopropyl palmitate | 8.0% |
| cetyl palmitate | 1.5% |
| silicone oil 100 | 0.5% |
| sorbitan monostearate | 3.0% |
| polysorbate 60 | 3.5% |
| 1,2-propylene glycol PH | 20.0% |
| acrylic acid polymer | 0.5% |
| triethanolamine | 0.7% |
| water, demineralised, to make up to | 100.0% |

The acrylic acid polymer is suspended in a mixture of demineralised water and 1,2-propylene glycol. Triethanolamine is then added while stirring to produce a glutinous liquid. A mixture of isopropyl palmitate, cetyl palmitate, silicone oil, sorbitan monostearate and polysorbate is heated to approximately 75° and incorporated by stirring into the glutinous liquid likewise heated to approximately 75°. The cream base, cooled to room temperature, is then used to produce a concentrate with the active substance. The concentrate is homogenised by means of a continuous homogeniser and then added in portions to the base.

EXAMPLE 25

A cream containing 5% 2-[4(5)-phenyl-5(4)-(1-oxido-3-pyridyl)-imidazol-2-yl]-2-methyl ethyl propionate can be manufactured as follows:

| Composition | |
| --- | --- |
| active substance | 5.0% |
| cetyl palmitate PH | 2.0% |
| cetyl alcohol PH | 2.0% |
| triglyceride mixture of saturated fatty acids of medium molecular weight | 5.0% |
| stearic acid | 3.0% |
| glycerine stearate pH | 4.0% |
| Cetomacrogol 1000 | 1.0% |
| microcrystalline cellulose | 0.5% |
| 1,2-propylene glycol, distilled | 20.0% |
| water, demineralised, to make up to | 100.0% |

Cetyl alcohol, cetyl palmitate, the triglyceride mixture, stearic acid and glycerine stearate are melted together. The microcrystalline cellulose is dispersed in part of the water. Cetomacrogol is dissolved in the remaining part of the water and the propylene glycol and the glutinous liquid are mixed in. The fatty phase is then added to the aqueous phase while stirring and the mixture is stirred until cold. Finally, the active substance is triturated with some of the base and then the product is incorporated into the remainder of the cream.

EXAMPLE 26

A transparent hydrogel containing 5% 2-[4(5)-phenyl-5(4)-(1-oxido-3-pyridyl)-imidazol-2-yl]-2-methyl ethyl propionate is manufactured as follows:

| Composition | |
| --- | --- |
| active substance | 5% |
| propylene glycol | 10-20% |
| isopropanol | 20% |
| hydroxypropylmethylcellulose | 2% |
| water to make up to | 100% |

The hydroxypropylmethylcellulose is swelled in water. The active substance is dissolved in a mixture of isopropanol and propylene glycol. The active substance solution is then mixed with the swollen cellulose derivative and, if desired, perfumes (0.1%) are added.

EXAMPLE 27

A transparent hydrogel containing 5% 2-[4(5)-(1-oxido-3-pyridyl)-imidazol-2-yl]-2-methyl ethyl propionate is manufactured as follows:

| Composition | |
| --- | --- |
| active substance | 5% |
| propylene glycol | 20% |
| isopropanol | 20% |
| acrylic acid polymer | 2% |
| triethanolamine | 3% |
| water to make up to | 100% |

Acrylic acid polymer and water are dispersed and neutralized with triethanolamine. The active substance is dissolved in a mixture of isopropanol and propylene glycol. The active substance solution is then mixed with the gel, in the course of which operation perfume (0.1%) may be added if desired.

EXAMPLE 28

A foam spray, containing 1% 2-[4(5)-phenyl-5(4)-(1-oxido-3-pyridyl)-imidazol-2-yl]-2-methylpropionic acid, can be manufactured as follows:

| Composition | |
| --- | --- |
| active substance | 1.00% |
| cetyl alcohol PH | 1.70% |
| paraffin oil, viscous | 1.00% |
| isopropyl myristate | 2.00% |
| Cetomacrogol 1000 | 2.40% |
| sorbitan monostearate | 1.50% |
| 1,2-propylene glycol PH | 5.00% |
| methyl Parabens | 0.18% |
| propyl Parabens | 0.02% |
| Chemoderm 314 | 0.10% |
| water, demineralised, to make up to | 100.00% |

Cetyl alcohol, paraffin oil, isopropyl myristate, Cetomacrogol and sorbitan monostearated are melted together. Methyl and propyl Parabens are dissolved in hot water. The melt and the solution are then mixed. The active substance, suspended in propylene glycol, is incorporated into the base. Chemoderm is then added and the whole is supplemented with water to the final weight.

Filling 20 ml of the mixture are filled into an aluminium can. The can is provided with a valve and the propellant gas is introduced under pressure.

EXAMPLE 29

With stirring, a solution of 2-malonic acid monoethyl ester chloride in 10 ml of anhydrous benzene is added at 10° C. over 1 hour to a solution of 5 g of α-hydroxybenzyl-3-pyridylketone (prepared in accordance with J. Chem. Soc. 1956, 2913) and 6 ml of triethylamine in 50 ml of anhydrous benzene. The mixture is stirred for 2 hours at 10° C. and then 60 ml of water are added. After extraction with two 60 ml portions of ethyl acetate, the organic phases are separated, combined, and washed with 30 ml of saturated sodium chloride solution, with two 30 ml portions of 1N sodium bicarbonate solution, and again with 30 ml of saturated sodium chloride solution. The organic phase is dried and evaporated to dryness at 30°C./11 torr. The residue, malonic acid monoethyl ester [1-phenyl-2-oxo-2-(3-pyridyl)] ethylester, is in the form of an oil.

A mixture of 3.5 g of malonic acid monoethyl ester [1-phenyl-2-oxo-2-(3-pyridyl)] ethyl ester, 1.15 g of ammonium acetate and 100 ml of glacial acetic acid is boiled for 2 hours under reflux and then evaporated to dryness at 50° C./11 torr. The residue is chromatographed over 120 g of silica gel. Fractions 1 to 4, each eluted with 300 ml of benzene/ethyl acetate/glacial acetic acid (94:5:1) are discarded. Fractions 5 to 9, eluted with the same mixture of solvents, are combined and evaporated to dryness under 11 torr. The residue contains ethyl 2-[4-(5)-phenyl-5(4)-(3-pyridyl)oxazol-2-yl]acetate as an oil (amorphous foam).

EXAMPLE 30

A solution of 16.6 g of ethyl 2-[4(5)-phenyl-5(4)-(3-pyridyl)oxazol-2-yl]acetate in 200 ml of methylene chloride is cooled to 0° C. To this cooled solution is added, with stirring, a solution of m-chloroperbenzoic acid in 200 ml of methylene chloride. The mixture is stirred for 1 hour at 0° C. and to it is then added a further solution of 11.3 g of m-chloroperbenzoic acid in 200 ml of methylene chloride. The mixture is then stirred for ½ hour at 0° C. and extracted with 50 ml of 2N potassium carbonate solution and 50 ml of water. The methylene chloride solution is separated, dried over magnesium sulfate and evaporated to dryness under 11 torr. The residue is chromatographed over 500 g of silica gel. Fractions 1 to 4, each eluted with 800 ml of chloroform/methanol (99:1), are discarded. Fractions 5 to 12, each eluted with 800 ml of chloroform/methanol (99:1), are combined and evaporated to dryness under 11 torr. The residue, ethyl 2-[4(5)-phenyl-5(4)-(1-oxido-3-pyridyl)oxazol-2-yl]acetate, is an oil (amorphous foam).

EXAMPLE 31

The following compounds are prepared by procedures similar to those described in Examples 29 or 30:

ethyl 2-[4(5)-phenyl-5(4)-(3-pyridyl)oxazol-2-yl]-2-methylpropionate, oil (amorphous foam),
ethyl 2-[4(5)-phenyl-5(4)-(3-pyridyl)oxazol-2-yl]-2-allyl-acetate,
1-[4(5)-phenyl-5(4)-(3-pyridyl)oxazol-2-yl]-1-carboethoxy-cyclopentane,
ethyl 2-[4(5)-(p-methoxyphenyl)-5(4)-(3-pyridyl)oxazol-2-yl]-2-methylpropionate,
ethyl 2-[4(5)-phenyl-5(4)-(1-oxido-3-pyridyl)oxazol-2-yl)-2-methylpropionate, oil (amorphous foam),
ethyl 2-[(4(5)-phenyl-5(4)-(3-pyridyl)oxazol-2-yl]-propionate,
ethyl 2-[4(5)-(p-chlorophenyl)-5(4)-(3-pyridyl)oxazol-2-yl]-2-methylpropionate, oil (amorphous foam),
ethyl 2-[4(5)-phenyl-5(4)-(4-pyridyl)oxazol-2-methylpropionate,
ethyl 2-[4(5)-(1-oxido-4pyridyl)oxazol-2-yl]-2-methylpropionate,
ethyl 2-[4(4)-(p-hydroxyphenyl)-5(4)-(3-pyridyl)oxazol-2-yl]-2-methylpropionate, oil (amorphous foam),
pivaloyloxymethyl 2-[4(5)-phenyl-5(4)-(3pyridyl)oxazol-2-yl]-2-methylpropionate, oil (amorphous foam).

I claim:
1. A compound of the formula I

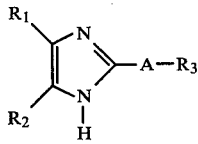

in which
one of the radicals $R_1$ and $R_2$ represent pyrrolyl, furyl, thienyl, pyridyl, 1-oxidopyridyl or pyrimidyl each of which are unsubstituted or substituted by halogen, lower alkyl, hydroxy, lower alkoxy, and/or lower alkanoyloxy,
and the other of the radicals $R_1$ and $R_2$ represents phenyl, pyrrolyl, furyl, thienyl, pyridyl, 1-oxidopyridyl or pyrimidyl each of which is unsubstituted or substituted by halogen, lower alkyl, hydroxy, lower alkoxy and/or lower alkanoyloxy;
A represents lower alkylene, lower alkylidene, lower alkenylene, lower alkenylidene, cycloalkylene, cycloalkylidene or cycloalkyl-lower alkylidene; and
$R_3$ represents carboxy, carboxy esterified by a lower alkanol, by a 3- to 8-membered cycloalkanol, by phenol, by a hydroxypyridine or by a substituted phenol or substituted hydroxypyridine, or represents carbamoyl or carbamoyl mono-substituted by hydroxy, by amino, by phenyl or by substituted phenyl, or represents carbamoyl mono- or di-substituted by lower alkyl or carbamoyl di-substituted by 4- to 7-membered alkylene or 3-aza-, 3-lower alkyl-aza-, 3-oxa- or 3-thiaalkylene, wherein said lower alkanol and said cycloalkanol can be unsubstituted or substituted by hydroxy, mercapto, optionally substituted phenyl, lower alkoxy, phenyl-lower alkoxy optionally substituted in the phenyl moiety, lower alkylthio, phenyl-lower alkylthio optionally substituted in the phenyl moiety, hydroxy-lower alkoxy, lower alkoxy-lower alkoxy, phenyl-lower alkoxy-lower alkoxy optionally substituted in the phenyl moiety, carboxy-lower alkoxy, lower alkoxycarbonyl-lower alkoxy, or lower alkoxycarbonyl-lower alkoxy containing optionally substituted phenyl, or lower alkanoyloxy, and wherein substituted phenyl, phenol or hydroxypyridine can each be substituted by lower alkyl, lower alkoxy, halogen and/or trifluoromethyl, their isomers and salts thereof.

2. Compounds according to claim 1 of the formula I in which one of the radicals $R_1$ and $R_2$ represents pyridyl or 1-oxido-pyridyl, each of which can be unsubstituted and/or substituted by halogen, hydroxy, lower alkyl, lower alkoxy and/or lower alkanoyloxy and the other represents phenyl, pyridyl or 1-oxidopyridyl each of which can be unsubstituted or substituted by halogen, hydroxy, lower alkyl, lower alkoxy and/or lower alkanoyloxy, A represents lower alkylene having up to and including 4 carbon atoms, lower alkylidene having up to and including 7 carbon atoms, lower alkenylene having up to and including 4 carbon atoms, lower alkenylidene having up to and including 7 carbon atoms, 3- to 8-membered cycloalkylene, 3- to 8-membered cycloalkylidene, or cycloalkyl-lower alkylidene having up to and including 7 carbon atoms in the alkylidene moiety and having a 3- to 8-membered cycloalkyl moiety, and $R_3$ represents carboxy, carboxy esterified by a lower alkanol, by a 3- to 8membered cycloalkanol, by phenol or by a substituted phenol, or represents carbamoyl, N-mono-, N,N-di-lower alkylcarbamoyl, pyrrolidino-, piperidino-, morpholino-, piperazino-, 4-lower alkylpiperazino-, thimorpholino- or anilinocarbonyl, or anilinocarbonyl substituted by lower alkyl, lower alkoxy and/or halogen, wherein the lower alkanol or cycloalkanol can be unsubstituted or substituted by hydroxy, mercapto, phenyl, substituted phenyl, lower alkoxy, phenyl-lower alkoxy, phenyl-lower alkoxy substituted in the phenyl moiety, lower alkylthio, phenyl-lower alkylthio, phenyl-lower alkylthio substituted in the phenyl moiety, hydroxy-lower alkoxy, lower alkoxy-lower alkoxy, phenyl-lower alkoxy-lower alkoxy, phenyl-lower alkoxy-lower alkoxy substituted in the phenyl moiety, carboxy-lower alkoxy, lower alkoxycarbonyl-lower alkoxy, or lower alkoxycarbonyl-lower alkoxy containing optionally substituted phenyl, or lower alkanoyloxy, and wherein substituted phenol or phenyl can each be substituted by lower alkyl, lower alkoxy, halogen and/or trifluoromethyl, their isomers and their pharmaceutically acceptable salts.

3. Compounds according to claim 1 of the formula I in which one of the radicals $R_1$ and $R_2$ represents phenyl or phenyl substituted by halogen having an atomic number of up to and including 35, by hydroxy, by lower alkyl having up to and including 4 carbon atoms, and/or by lower alkoxy having up to and including 4 carbon atoms, and the other represent pyridyl or 1-oxidropyridyl each of which can be unsubstituted or substituted by halogen having an atomic number of up to and including 35, by hydroxy, and/or by lower alkoxy having up to and including 4 carbon atoms, A represents lower alkylene having up to and including 4 carbon atoms, lower alkylidene having up to and including 7 carbon atoms, lower alkenylidene having up to and including 7 carbon atoms, or 3- to 8-membered cyclo-lower alkylidene, and $R_3$ represents carboxy, lower alkoxycarbonyl having up to and including 5 carbon atoms, carbamoyl, N-mono-lower alkylcarbamoyl having up to and including 4 carbon atoms in the lower alkyl, or N,N-di-lower alkylcarbamoyl having up to and including 4 carbon atoms in each lower alkyl, wherein the lower alkoxycarbonyl can be substituted by lower alkanoyloxy having up to and including 5 carbon atoms, their isomers and their pharmaceutically acceptable salts.

4. Compounds according to claim 1 of the formula I in which one of the radicals $R_1$ and $R_2$ represents phenyl or phenyl substituted by halogen having an atomic number of up to and including 35, by hydroxy or by lower alkoxy having up to and including 4 carbon atoms, and the other represents pyridyl or 1-oxidopyridyl, A represents lower alkylidene having up to and including 4 carbon atoms and containing a quaternary carbon atom, wherein the quaternary carbon atom is bonded directly to the imidazole ring, and $R_3$ represents lower alkoxycarbonyl having up to and including 5 carbon atoms, their isomers and their pharmaceutically acceptable salts.

5. Compounds according to claim 1 of the formula I in which one of the radicals $R_1$ and $R_2$ represents phenyl and the other represents 1-oxidopyridyl, A represents 2,2-propylidene and $R_3$ represents lower alkoxycarbonyl having up to and including 5 carbon atoms, their isomers and their pharmaceutically acceptable salts.

6. A compound as claimed in claim 1 being 2-[4(5)-phenyl-5(4)-(3-pyridyl)-imidazol-2-yl]-2-methyl ethyl propionate or a pharmaceutically acceptable salt thereof.

7. A compound as claimed in claim 1 being 2-[4(5)-phenyl-5(4)-(3-pyridyl)-imidazol-2-yl]-2-allyl ethyl acetate or a pharmaceutically acceptable salt thereof.

8. A compound as claimed in claim 1 being 1-[4(5)-phenyl-5(4)-(3-pyridyl)-imidazol-2-yl]-1-ethoxycarbonylcyclopentane or a pharmaceutically acceptable salt thereof.

9. A compound as claimed in claim 1 being 2-[4 (5)-(p-methoxyphenyl)-5(4)-(3-pyridyl)-imidazol-2-yl]-2-methyl ethyl propionate or a pharmaceutically acceptable salt thereof.

10. A compound as claimed in claim 1 being 2-]4(5)-phenyl-5(4)-(1-oxido-3-pyridyl)-imidazol-2-yl]-2-methyl ethyl propionate or a pharmaceutically acceptable salt thereof.

11. A compound as claimed in claim 1 being 2-[4(5)-phenyl-5(4)-(3-pyridyl)-imidazol-2-yl]-ethyl propionate or a pharmaceutically acceptable salt thereof.

12. A compound as claimed in claim 1 being 2-[4(5)-(p-chlorophenyl)-5(4)-(3-pyridyl)-imidazol-2 yl]-2-methyl ethyl propionate or a pharmaceutically acceptable salt thereof.

13. A compound as claimed in claim 1 being 2-[4(5)-phenyl-5(4)-(4-pyridyl)-imidazol-2-yl]-2-methyl ethyl propionate or a pharmaceutically acceptable salt thereof.

14. A compound as claimed in claim 1 being 2-[4(5)-phenyl-5(4)-(1-oxido-4-pyridyl)-imidazol-2-yl]-2-methyl ethyl propionate or a pharmaceutically acceptable salt thereof.

15. A compound as claimed in claim 1 being 2-[4(5)-(p-hydroxyphenyl)-5(4)-(3-pyridyl)-imidazol-2-yl]-2-methyl ethyl propionate or a pharmaceutically acceptable salt thereof.

16. A pharmaceutical composition comprising an antiphlogistically and/or anti-herpes effective amount of a compound as claimed in claim 1 together with a conventional pharmaceutial carrier.

17. A method for the treatment of inflammatory dermatoses and/or herpes infections comprising administering externally an antiphlogistically and/or anti-herpes effective amount of a compound as claimd in claim 1.

* * * * *